US011324622B1

(12) United States Patent
Solotoff

(10) Patent No.: US 11,324,622 B1
(45) Date of Patent: May 10, 2022

(54) BACK BRACE BELT AND APPARATUS, AND METHOD OF BELT LENGTH ADJUSTMENT THEREFOR

(71) Applicant: Brandon Solotoff, Boca Raton, FL (US)

(72) Inventor: Brandon Solotoff, Boca Raton, FL (US)

(73) Assignee: Preferred Prescription, Inc., Hollywood, FL (US)

( * ) Notice: Subject to any disclaimer, the term of this patent is extended or adjusted under 35 U.S.C. 154(b) by 106 days.

(21) Appl. No.: 16/986,459

(22) Filed: Aug. 6, 2020

Related U.S. Application Data

(60) Provisional application No. 62/884,271, filed on Aug. 8, 2019.

(51) Int. Cl.
*A61F 5/02* (2006.01)

(52) U.S. Cl.
CPC .............. *A61F 5/024* (2013.01); *A61F 5/028* (2013.01)

(58) Field of Classification Search
CPC ... A61F 5/02–03; A61F 5/24–34; A41H 1/00; A41H 1/02; A41H 1/06; A41F 9/00–025; A45F 3/14–15; A61B 5/107; A61B 5/1072; G01B 3/00; G01B 3/10–1004; G01B 3/1056; G01B 3/1084; G01B 3/1089; G01B 5/00–004; G01B 5/02–025; G01B 5/08
See application file for complete search history.

(56) References Cited

U.S. PATENT DOCUMENTS

| 321,145 A | 6/1885 | Spencer |
| 368,699 A | 8/1887 | Zervas |
| 386,642 A | 7/1888 | Mann |
| 507,172 A | 10/1893 | Shelden |

(Continued)

FOREIGN PATENT DOCUMENTS

| CN | 201101603 Y | 8/2008 |
| CN | 202068989 U | 12/2011 |

(Continued)

OTHER PUBLICATIONS

US 9,665,761 B2, 05/2017, Joseph (withdrawn)

(Continued)

*Primary Examiner* — Michelle J Lee
(74) *Attorney, Agent, or Firm* — Thomas A. O'Rourke; Bodner & O'Rourke, LLP

(57) ABSTRACT

A back brace includes: a back plate; left and right cord plates each slidably mounted to left and right sides of the back plate, respectively, and to which first and second flexible belt members are respectively secured; and a cord guide arrangement for each plate to particularly direct first and second cords. Each of the left and right cord plates include a pair of concentric cord guides, each of which are formed of a circular segment that is 180 degrees or less. The first cord is selectively wound around the pair of concentric cord guides on the upper portions of the left and right cord plates, while the second cord is selectively wound around the pair of concentric cord guides on the lower portion of the cord plates, so pulling on the cords provides a mechanical advantage to buckle the plate to exert a compressive force on the patient's torso.

14 Claims, 23 Drawing Sheets

(56) References Cited

U.S. PATENT DOCUMENTS

| | | |
|---|---|---|
| 571,749 A | 11/1896 | Colton |
| 601,446 A | 3/1898 | Mestler |
| 616,196 A | 12/1898 | Medbury |
| 629,900 A | 8/1899 | Fosburgh |
| 639,072 A | 12/1899 | Lyons |
| 664,250 A | 12/1900 | Fitzpatrick |
| 709,055 A | 9/1902 | Sheldon |
| 714,124 A | 11/1902 | Adams |
| 772,926 A | 10/1904 | Colton |
| 888,490 A | 5/1908 | Haas |
| 894,066 A | 7/1908 | Scarpa |
| 1,008,500 A | 11/1911 | Thornton |
| 1,184,581 A | 5/1916 | Sigurini |
| 1,316,915 A | 9/1919 | Meyer |
| 1,393,188 A | 10/1921 | Whiteman |
| 1,558,661 A | 10/1925 | Yeganian |
| 1,581,791 A | 4/1926 | Davison |
| 1,755,641 A | 4/1930 | Foulke |
| 1,948,785 A | 2/1934 | Dondelinger |
| 1,981,157 A | 11/1934 | Walter |
| 2,016,484 A | 4/1936 | Le May |
| 2,100,964 A | 11/1937 | Kendrick |
| 2,117,309 A | 5/1938 | Fritsch |
| 2,181,689 A | 11/1939 | Bell |
| 2,219,475 A | 10/1940 | Flaherty |
| 2,316,102 A | 4/1943 | Preston |
| 2,409,381 A | 10/1946 | Pease |
| 2,554,337 A | 5/1951 | Lampert |
| 2,749,550 A | 6/1956 | Pease |
| 2,793,368 A | 5/1957 | Nouel |
| 2,808,050 A | 10/1957 | Ward |
| 2,828,737 A | 4/1958 | Hale |
| 2,906,260 A | 9/1959 | Myers |
| 3,029,810 A | 4/1962 | Martin |
| 3,095,875 A | 7/1963 | Davidson |
| 3,096,760 A | 7/1963 | Nelkin |
| 3,274,996 A | 9/1966 | Jewett |
| 3,282,264 A | 11/1966 | Connelly |
| 3,351,053 A | 11/1967 | Stuttle |
| 3,371,351 A | 3/1968 | Allain |
| 3,420,230 A | 1/1969 | Ballard |
| 3,434,469 A | 3/1969 | Swift |
| 3,509,875 A | 5/1970 | Richter |
| 3,548,817 A | 12/1970 | Mittasch |
| 3,578,773 A | 5/1971 | Schultz |
| 3,603,316 A | 9/1971 | Lehman |
| 3,771,513 A | 11/1973 | Velazquez |
| 3,889,664 A | 6/1975 | Heuser |
| 3,902,503 A | 9/1975 | Gaylord |
| 3,920,008 A | 11/1975 | Lehman |
| 3,926,182 A | 12/1975 | Stabholz |
| 3,926,183 A | 12/1975 | Spiro |
| 3,927,665 A | 12/1975 | Wax |
| 3,945,376 A | 3/1976 | Kuchnegger |
| 4,099,524 A | 7/1978 | Cueman |
| 4,173,973 A | 11/1979 | Hendricks |
| 4,175,553 A | 11/1979 | Rosenberg |
| 4,230,101 A | 10/1980 | Gold |
| 4,285,336 A | 8/1981 | Oebser |
| 4,383,523 A | 5/1983 | Schurman |
| 4,475,543 A | 10/1984 | Brooks |
| 4,508,110 A | 4/1985 | Modglin |
| 4,559,933 A | 12/1985 | Batard |
| 4,572,167 A | 2/1986 | Brunswick |
| 4,574,789 A | 3/1986 | Forster |
| 4,640,269 A | 2/1987 | Goins |
| 4,691,696 A | 9/1987 | Farfan de los Godos |
| 4,696,291 A | 9/1987 | Tyo |
| 4,735,004 A | 4/1988 | Dodge |
| 4,750,480 A | 6/1988 | Jenness |
| 4,768,499 A | 9/1988 | Kemp |
| 4,807,605 A | 2/1989 | Mattingly |
| 5,072,725 A | 12/1991 | Miller |
| 5,111,807 A | 5/1992 | Spahn |
| 5,121,741 A | 6/1992 | Bremer |
| 5,127,897 A | 7/1992 | Roller |
| 5,135,471 A | 8/1992 | Houswerth |
| 5,176,131 A | 1/1993 | Votel |
| 5,179,942 A | 1/1993 | Drulias |
| D334,063 S | 3/1993 | DeWall |
| 5,195,948 A | 3/1993 | Hill |
| 5,203,765 A | 4/1993 | Friddle |
| 5,226,874 A | 7/1993 | Heinz |
| 5,232,424 A | 8/1993 | Pearson |
| 5,241,704 A | 9/1993 | Sydor |
| 5,257,419 A | 11/1993 | Alexander |
| 5,259,831 A | 11/1993 | LeBron |
| 5,259,833 A | 11/1993 | Barnett |
| 5,267,948 A | 12/1993 | Elliot |
| 5,295,947 A | 3/1994 | Muncy |
| 5,307,521 A | 5/1994 | Davis |
| 5,346,461 A | 9/1994 | Heinz |
| 5,362,304 A | 11/1994 | Vam |
| 5,363,863 A | 11/1994 | Lelli |
| 5,388,274 A | 2/1995 | Glover |
| 5,399,150 A | 3/1995 | Saunders |
| 5,399,154 A | 3/1995 | Kipnis |
| 5,421,809 A | 6/1995 | Rise |
| 5,433,697 A | 7/1995 | Cox |
| 5,437,614 A | 8/1995 | Grim |
| 5,449,338 A | 9/1995 | Trudell |
| 5,450,858 A | 9/1995 | Zablotsky |
| 5,466,214 A | 11/1995 | Calderon-Garciduenas |
| 5,484,395 A | 1/1996 | DeRoche |
| 5,500,959 A | 3/1996 | Yewer |
| 5,503,620 A | 4/1996 | Danziger |
| 5,533,961 A | 7/1996 | Iwata |
| 5,548,843 A | 8/1996 | Chase |
| 5,551,085 A | 9/1996 | Leighton |
| 5,560,046 A | 10/1996 | Iwamasa |
| 5,586,969 A | 12/1996 | Yewer |
| 5,599,287 A | 2/1997 | Beczak |
| 5,620,412 A | 4/1997 | Modglin |
| 5,634,891 A | 6/1997 | Beczak |
| 5,690,609 A | 11/1997 | Heinze |
| 5,718,670 A | 2/1998 | Bremer |
| 5,722,940 A | 3/1998 | Gaylord |
| 5,728,056 A | 3/1998 | Seriguchi |
| 5,785,672 A * | 7/1998 | Mattison ................ A61F 5/028 |
| | | 128/101.1 |
| RE35,940 E | 10/1998 | Heinz |
| 5,816,251 A | 10/1998 | Glisan |
| 5,853,378 A | 12/1998 | Mpdglin |
| 5,853,379 A | 12/1998 | Ostojic |
| 5,911,697 A | 6/1999 | Biederman |
| 6,039,707 A | 3/2000 | Crawford |
| 6,066,108 A | 5/2000 | Lundberg |
| 6,099,490 A | 8/2000 | Turtzo |
| 6,102,879 A | 8/2000 | Christensen |
| 6,117,096 A | 9/2000 | Hassard |
| 6,129,691 A | 10/2000 | Ruppert |
| 6,190,343 B1 | 2/2001 | Heinz |
| 6,213,968 B1 | 4/2001 | Heinz |
| 6,322,529 B1 * | 11/2001 | Chung .................... A61F 5/028 |
| | | 2/319 |
| 6,471,665 B1 | 10/2002 | Milbourn |
| 6,478,759 B1 | 11/2002 | Modglin |
| 6,494,853 B1 | 12/2002 | Rossi |
| 6,500,137 B1 | 12/2002 | Molino |
| 6,503,215 B1 | 1/2003 | Reinhardt |
| 6,517,502 B2 | 2/2003 | Heyman |
| 6,540,703 B1 | 4/2003 | Lerman |
| 6,602,214 B2 | 8/2003 | Heinz |
| 6,623,419 B1 | 9/2003 | Smith |
| 6,676,617 B1 | 1/2004 | Miller |
| 6,676,620 B2 | 1/2004 | Schwenn |
| 6,755,799 B2 | 6/2004 | Toda |
| 6,790,191 B1 | 9/2004 | Hendricks |
| D499,806 S | 12/2004 | Machin |
| D501,078 S | 1/2005 | Cabana |
| 6,942,630 B2 | 9/2005 | Behan |
| 6,951,547 B1 | 10/2005 | Park |
| 6,962,572 B1 | 11/2005 | Zahiri |
| 6,964,644 B1 | 11/2005 | Garth |

(56) References Cited

U.S. PATENT DOCUMENTS

| | | |
|---|---|---|
| 7,001,348 B2 | 2/2006 | Garth |
| D518,895 S | 4/2006 | Weaver |
| 7,025,737 B2 | 4/2006 | Modglin |
| 7,083,585 B2 | 8/2006 | Latham |
| 7,101,348 B2 | 9/2006 | Garth |
| 7,118,543 B2 | 10/2006 | Telles |
| 7,128,724 B2 | 10/2006 | Marsh |
| 7,198,610 B2 | 4/2007 | Ingimundarson |
| 7,309,304 B2 | 12/2007 | Stewart |
| 7,316,660 B1 | 1/2008 | Modglin |
| 7,329,231 B2 | 2/2008 | Frank |
| 7,473,235 B2 | 1/2009 | Schwenn |
| 7,556,608 B2 | 7/2009 | Parizot |
| 7,597,672 B2 | 10/2009 | Kruijsen |
| 7,597,675 B2 | 10/2009 | Ingimundarson |
| 7,600,660 B2 | 10/2009 | Kasper |
| 7,662,121 B2 | 2/2010 | Zours |
| 7,727,172 B2 | 6/2010 | Wang |
| 7,785,282 B2 | 8/2010 | Rauch |
| 7,794,418 B2 | 9/2010 | Ingimundarson |
| 7,815,585 B2 * | 10/2010 | Vollbrecht .............. A61F 5/028 602/19 |
| 7,819,831 B2 | 10/2010 | Dellanno |
| 7,833,182 B2 | 11/2010 | Hughes |
| 7,871,388 B2 | 1/2011 | Brown |
| 7,905,849 B2 | 3/2011 | Park |
| D636,494 S | 4/2011 | Garth |
| D641,483 S | 7/2011 | Robertson |
| 8,057,417 B2 | 11/2011 | Imai |
| 8,066,654 B2 | 11/2011 | Sandifer |
| D654,180 S | 2/2012 | Weaver |
| 8,142,377 B2 | 3/2012 | Garth |
| 8,172,779 B2 | 5/2012 | Ingimundarson |
| 8,182,438 B2 | 5/2012 | Rumsey |
| D666,301 S | 8/2012 | Joseph |
| 8,235,925 B2 | 8/2012 | Cavalieri |
| 8,277,404 B2 | 10/2012 | Einarsson |
| 8,303,527 B2 | 11/2012 | Joseph |
| 8,308,670 B2 | 11/2012 | Sandifer |
| 8,328,742 B2 | 12/2012 | Bledsoe |
| 8,372,023 B2 * | 2/2013 | Garth ..................... A61F 5/028 602/19 |
| 8,382,693 B1 | 2/2013 | Guldalian |
| 8,409,122 B2 | 4/2013 | Cropper |
| 8,435,196 B2 | 5/2013 | Bannister |
| 8,449,484 B2 | 5/2013 | Johnson |
| 8,556,840 B2 | 10/2013 | Burke |
| 8,657,769 B2 | 2/2014 | Ingimundarson |
| 8,663,141 B2 | 3/2014 | Garth |
| 8,795,214 B1 | 8/2014 | Conti |
| 8,795,215 B2 | 8/2014 | Rossi |
| 8,808,213 B2 | 8/2014 | Hendricks |
| 8,864,695 B2 | 10/2014 | Thornton |
| 8,920,353 B2 | 12/2014 | Hinshon |
| 8,926,537 B2 | 1/2015 | Ingimundarson |
| 8,939,925 B2 | 1/2015 | Ingimundarson |
| 8,945,034 B2 | 2/2015 | Ingimundarson |
| 8,956,315 B2 | 2/2015 | Garth |
| 9,155,651 B2 | 10/2015 | Ochoa |
| 9,295,577 B2 | 3/2016 | Stier |
| 9,314,363 B2 | 4/2016 | Ingimundarson |
| 9,339,406 B2 | 5/2016 | Burke |
| 9,345,279 B2 | 5/2016 | Chao |
| 9,370,440 B2 | 6/2016 | Ingimundarson |
| 9,393,149 B2 | 7/2016 | Garth |
| 9,414,953 B2 | 8/2016 | Ingimundarson |
| 9,439,800 B2 | 9/2016 | Ingimundarson |
| 9,468,554 B2 | 10/2016 | Petursson |
| 9,554,935 B2 | 1/2017 | Ingimundarson |
| 9,572,705 B2 | 2/2017 | Ingimundarson |
| 9,636,247 B2 | 5/2017 | Miller |
| 9,795,500 B2 | 10/2017 | Ingimundarson |
| 9,872,794 B2 | 1/2018 | Ingimundarson |
| D816,234 S | 4/2018 | Calvello |
| 10,159,592 B2 | 12/2018 | Ingimundarson |
| 10,166,164 B2 | 1/2019 | Johnson |
| 2001/0008955 A1 | 7/2001 | Garth |
| 2002/0032397 A1 | 3/2002 | Coligado |
| 2003/0000986 A1 | 1/2003 | Smith |
| 2003/0125650 A1 | 7/2003 | Grosso |
| 2003/0220594 A1 | 11/2003 | Halvorson |
| 2004/0097857 A1 | 5/2004 | Reinecke |
| 2004/0132380 A1 | 7/2004 | Kihara |
| 2004/0133138 A1 | 7/2004 | Modglin |
| 2004/0143204 A1 | 7/2004 | Salmon |
| 2005/0067816 A1 | 3/2005 | Buckman |
| 2005/0137508 A1 | 6/2005 | Miller |
| 2005/0165338 A1 | 7/2005 | Iglesias |
| 2006/0206992 A1 | 9/2006 | Godshaw |
| 2006/0254598 A1 | 11/2006 | Saul |
| 2008/0262401 A1 | 11/2008 | Wagner |
| 2009/0030359 A1 | 1/2009 | Wilkenheiser |
| 2009/0082707 A1 | 3/2009 | Rumsey |
| 2009/0118655 A1 * | 5/2009 | Wang ...................... A61F 5/028 602/19 |
| 2009/0192425 A1 | 7/2009 | Garth |
| 2009/0204042 A1 * | 8/2009 | Park ........................ A61F 5/028 602/19 |
| 2009/0275871 A1 | 11/2009 | Liu |
| 2010/0100019 A1 * | 4/2010 | Chen ........................ A61F 5/03 602/19 |
| 2010/0168630 A1 | 7/2010 | Cropper |
| 2010/0268141 A1 | 10/2010 | Bannister |
| 2010/0318010 A1 | 12/2010 | Sandifer |
| 2012/0253251 A1 * | 10/2012 | Thornton ................. A61F 5/028 602/19 |
| 2013/0006158 A1 | 1/2013 | Ingimundarson |
| 2013/0178774 A1 | 7/2013 | Hayes |
| 2013/0190670 A1 | 7/2013 | Von Zieglauer |
| 2013/0237891 A1 * | 9/2013 | Fryman ................... A61F 5/028 602/19 |
| 2013/0289461 A1 | 10/2013 | Cropper |
| 2014/0142485 A1 | 5/2014 | Berry |
| 2014/0188023 A1 | 7/2014 | Modglin |
| 2014/0276258 A1 | 9/2014 | Hall |
| 2014/0276308 A1 | 9/2014 | DiAngelo |
| 2014/0303536 A1 | 10/2014 | Guldalian |
| 2014/0364786 A1 | 12/2014 | Haider |
| 2018/0221189 A1 | 8/2018 | Garth |

FOREIGN PATENT DOCUMENTS

| | | |
|---|---|---|
| DE | 1197192 B | 7/1965 |
| DE | 6943014 U | 2/1970 |
| DE | 20204747 U1 | 7/2002 |
| DE | 10329454 A1 | 1/2005 |
| DE | 202005007124 U1 | 6/2005 |
| DE | 102012011742 A1 | 12/2013 |
| EP | 1159940 A2 | 12/2001 |
| EP | 1236412 A1 | 9/2002 |
| EP | 1743608 A2 | 1/2007 |
| FR | 1104562 A | 11/1955 |
| GB | 909970 A | 11/1962 |
| JP | 2009082697 A | 4/2009 |
| KR | 101184287 B1 | 9/2012 |
| WO | WO 2006/121413 | 11/2006 |
| WO | WO 2007/003148 | 1/2007 |
| WO | WO 2009/017499 | 2/2009 |
| WO | WO 2009/017949 | 2/2009 |
| WO | WO 2009/052031 | 4/2009 |
| WO | WO 2014/074855 | 5/2014 |
| WO | WO 2016/138215 | 9/2016 |

OTHER PUBLICATIONS

Press Fit Forces Stress Design Calculator, Jun. 18, 2018, available at: www.engineersedge.com/calculators/machine-design/press-fit/press-fit.htm.

"Three General Types of Fit," available at www.mmto.org/dclark/Reports/Encoder%20Upgrade/fittolerences%20%5BRead-Only%5D.pdf., Jul. 8, 2019.

(56) References Cited

OTHER PUBLICATIONS

"Engineering Fit," available at: https://en.wikipedia.org/wiki/Engineering_fit, Jul. 8, 2019.

* cited by examiner

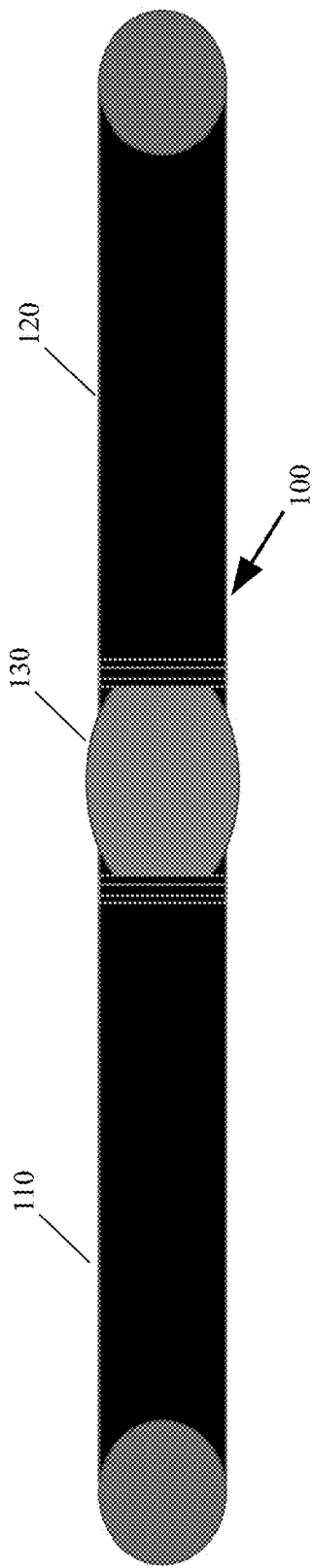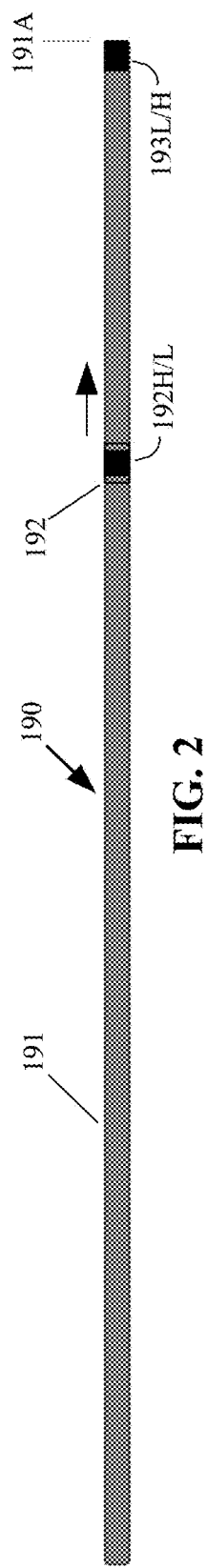

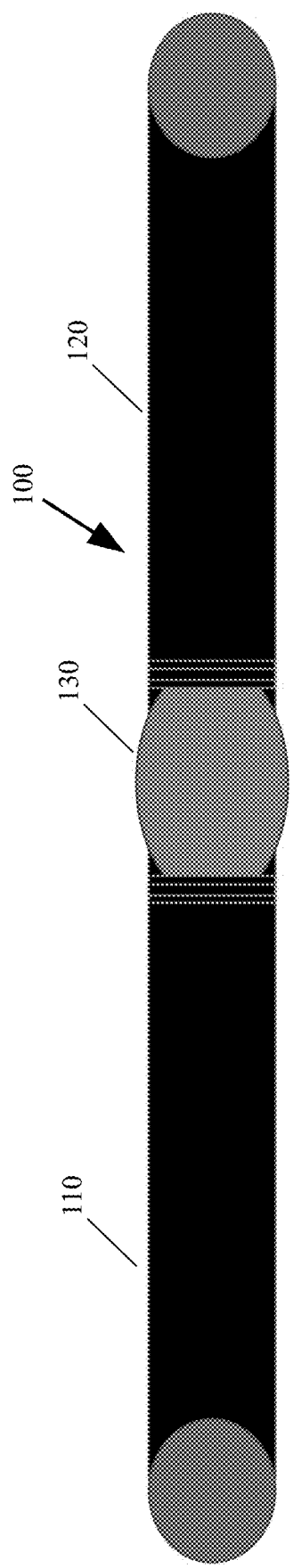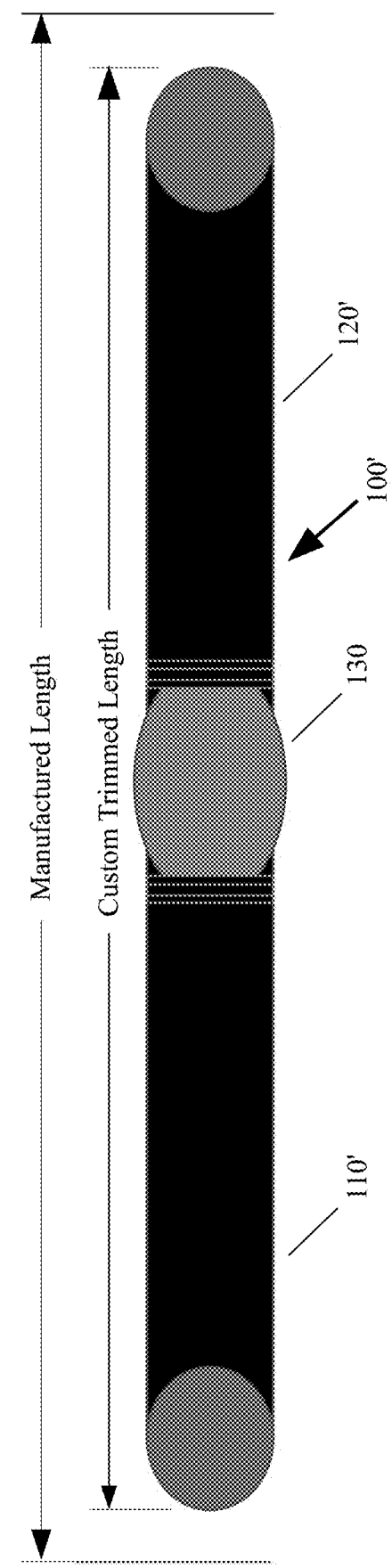
FIG. 9
FIG. 10

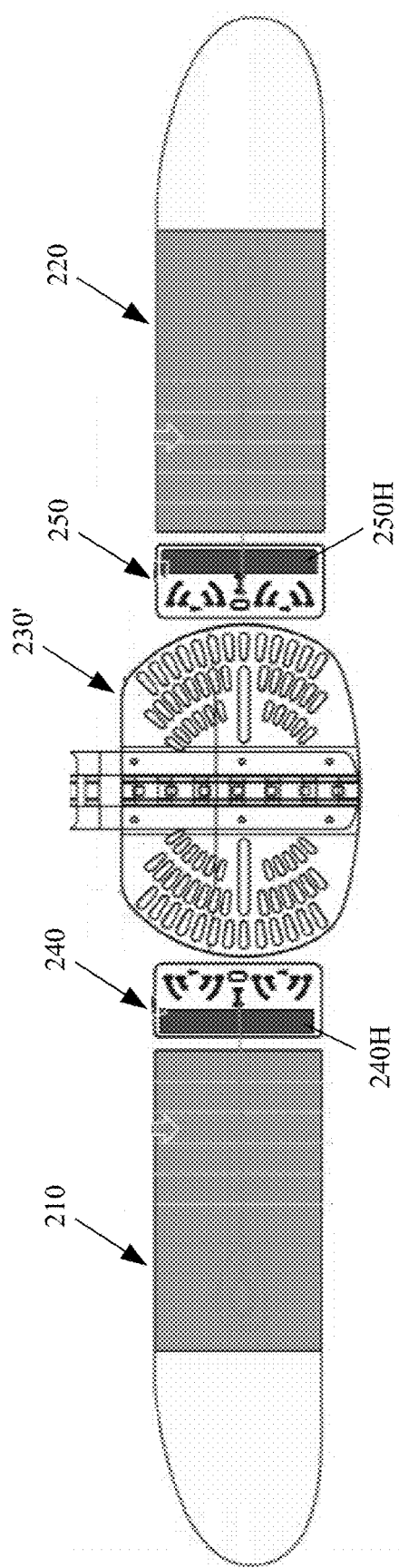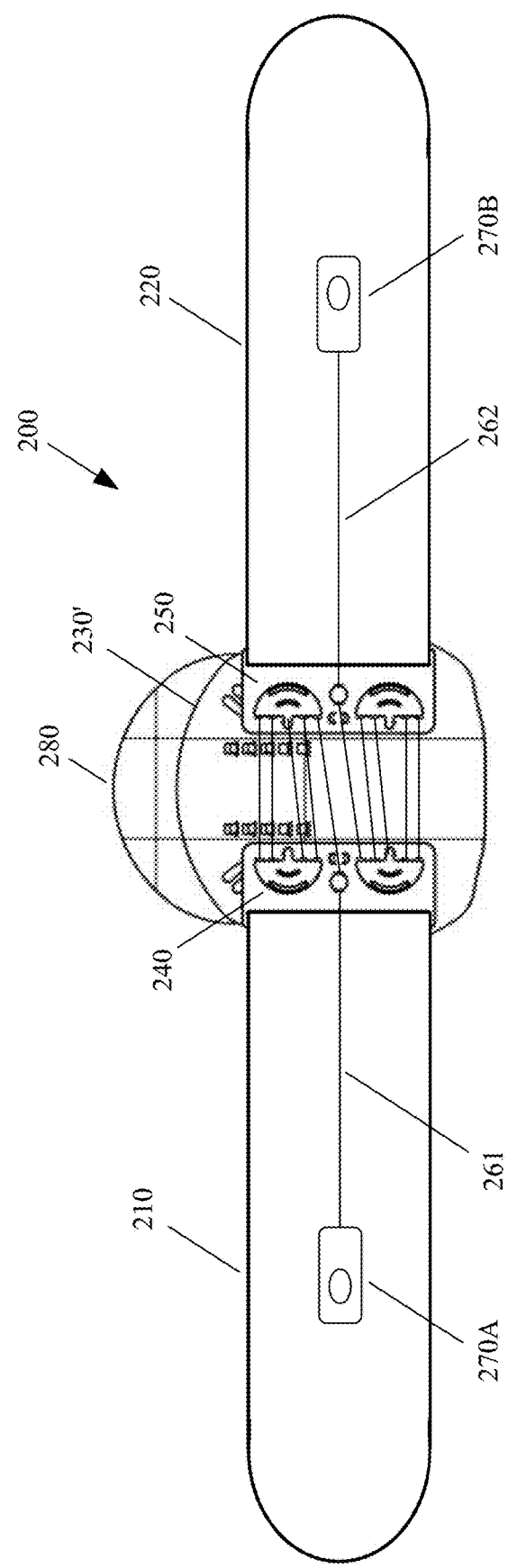

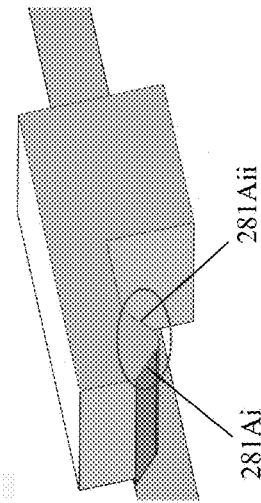
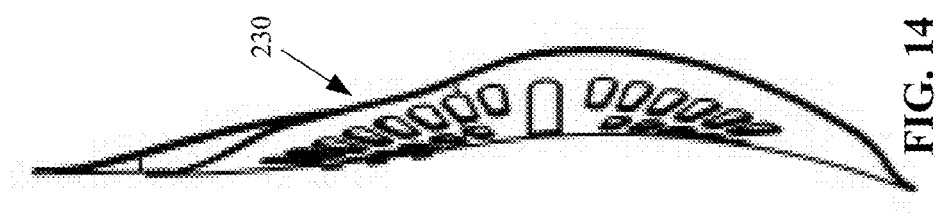
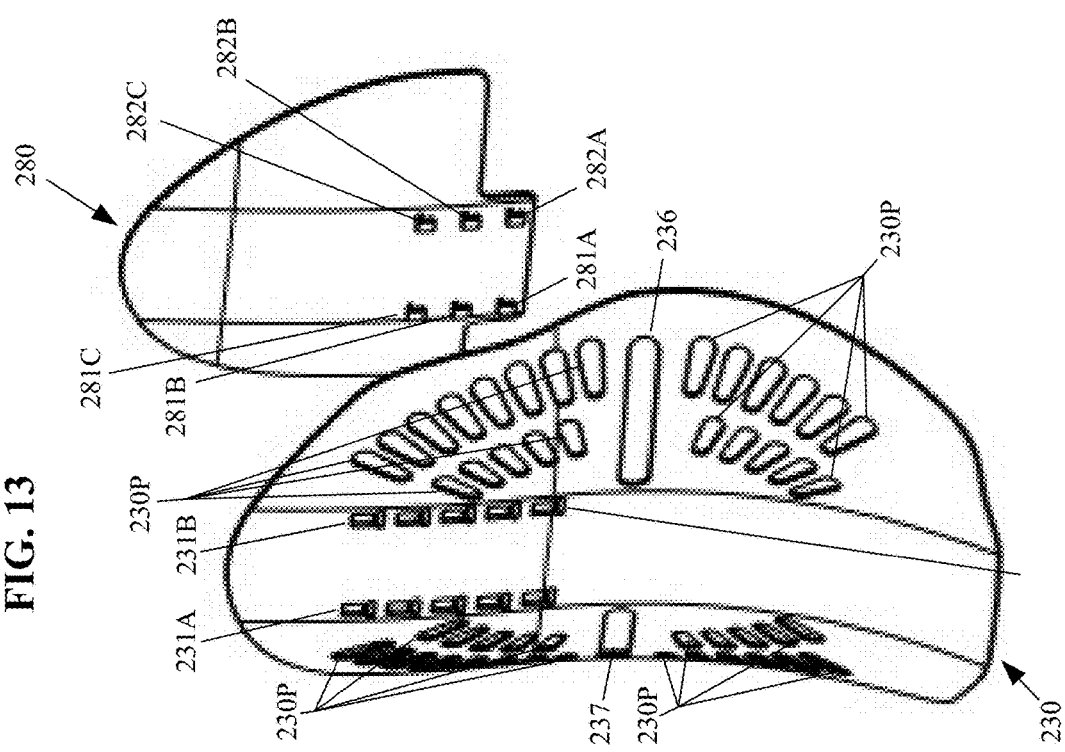

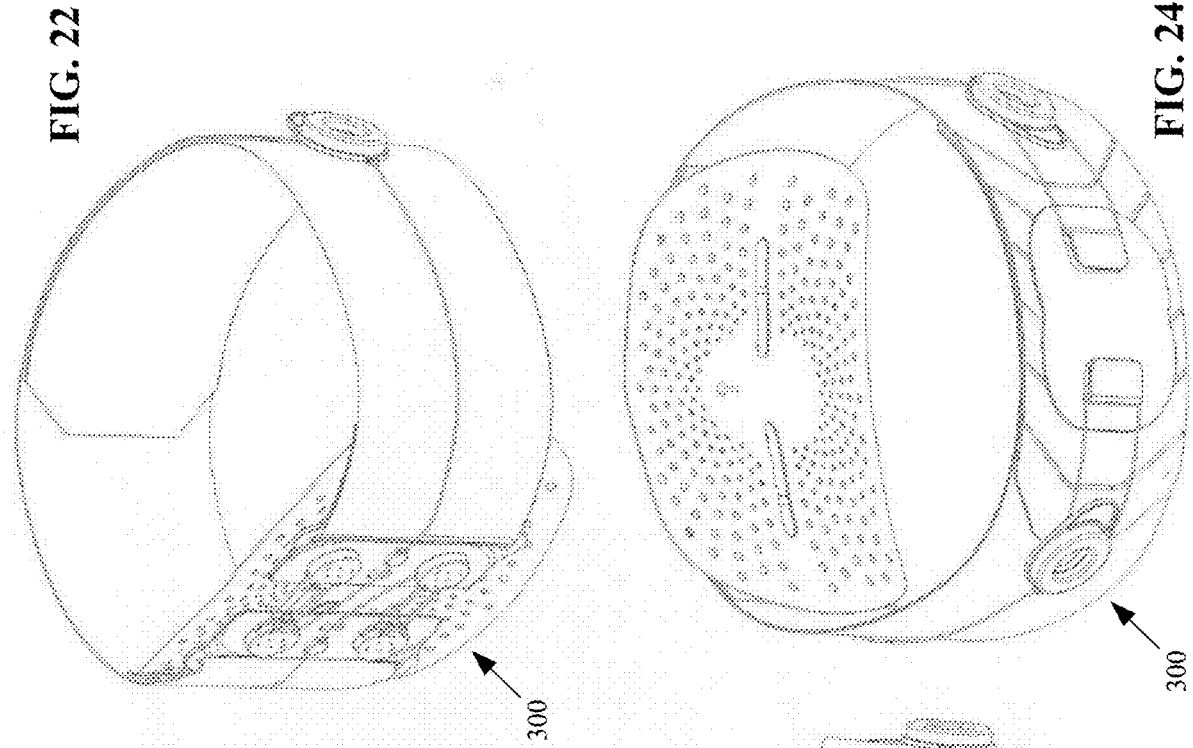
FIG. 22
FIG. 24
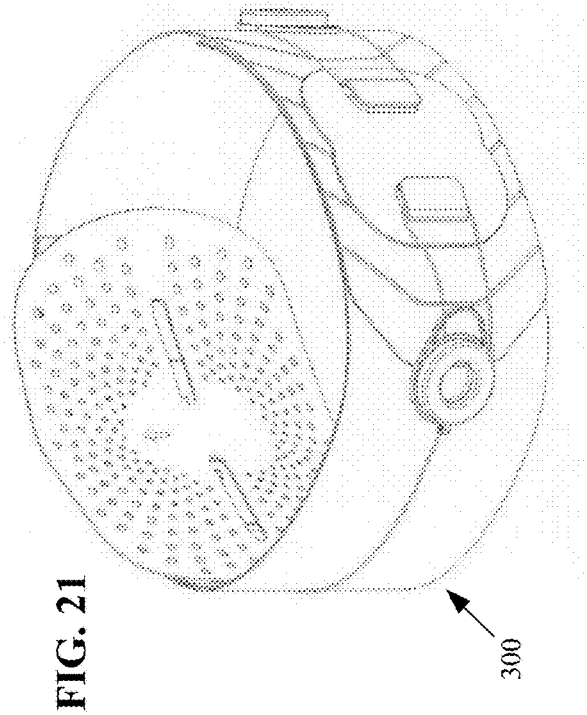
FIG. 21
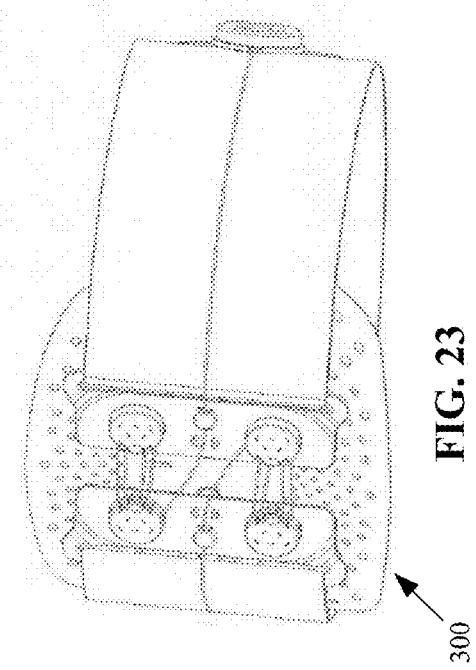
FIG. 23

BACK BRACE BELT AND APPARATUS, AND METHOD OF BELT LENGTH ADJUSTMENT THEREFOR

CROSS REFERENCES TO RELATED APPLICATIONS

This application claims priority on U.S. Provisional Application Ser. No. 62/884,271, filed on Aug. 8, 2019, the disclosures of which are incorporated herein by reference.

FIELD OF THE INVENTION

The subject technology relates generally to an orthopedic device for treatment of the back, and more particularly to a back brace that includes a plate member and belt portions coupled to the plate member, and a method of adjusting the length of the belt portions to fit various sized persons.

BACKGROUND OF THE INVENTION

There are many causes of back pain, particularly with respect to lower back aches. Many back issues are commonly treated with physical therapy, and/or non-steroidal anti-inflammatory drugs including diclofenac, ibuprofen, and naproxen. In addition, a back brace may be worn to assist with the healing of back injuries/issues (e.g., for disk problems such as spinal stenosis and herniated disks, spinal fractures, sciatica, etc.). A back brace may also be worn to decrease the chance of further injury, to help control pain, to support weakened muscles, and to promote good posture.

A typical back brace provides support through use of a wide belt (and sometimes additional apparatus) that may encircle and tend to immobilize the lower back, by generally limiting or preventing flexion, extension, etc. The additional apparatus may be a flexible plate secured to the belt, and two pulley arrangements on respective sides of the plate, where a cord or cords may loop around the pulleys and may be pulled to deform the plate into further contact with the wearer's back. The ends of the cord may have a handle that may attach to the belt when not being actuated.

Since many people that wear such back braces have very different sized body frames (e.g., waist sizes), the belt must be configured to accommodate those various sizes. Among the problems with prior art back braces is that they typically are the wrong or less than optimal size for the particular person, it is the wrong fit, and as soon as the handles/cables and pulleys are used to deform the plate, the support thereby provided is no longer in the correct place.

The apparatus and method disclosed herein are devised to easily adjust, and configure (i.e., custom tailor) a belt of a back brace according to the individual size of the wearer. The apparatus disclosed herein is also particularly configured to provide a better fit for each individual wearer, and to provide better contact and proper support when the handles/cables are used in conjunction with pulleys to deform the back plate.

Braces that may be related may be shown within the following U.S. patent and patent application Publication Numbers: U.S. Pat. No. 6,602,214 to Heinz; U.S. Pat. No. 6,213,968 to Heinz; U.S. Pat. No. 6,517,502 to Heyman; U.S. Pat. No. 6,676,620 to Schwenn; U.S. Pat. No. 6,951,547 to Park; U.S. Pat. No. 7,001,348 to Garth; U.S. Pat. No. 7,727,172 to Wang; U.S. Pat. No. 7,905,849 to Park; U.S. Pat. No. 8,142,377 to Garth; 2010/0318010 by Sandifer; U.S. Pat. No. 8,172,779 to Ingimundarson; U.S. Pat. No. 8,409,122 to Cropper; U.S. Pat. No. 8,795,214 to Conti; and U.S. Pat. No. 9,393,149 to Garth.

It is noted that citing herein of any patents, published patent applications, and non-patent literature is not an admission as to any of those references constituting prior art with respect to the disclosed and/or claimed apparatus.

OBJECTS OF THE INVENTION

It is an object of the invention to provide a brace that may be worn to provide support to the wearer's back.

It is another object of the invention to provide a back brace with a first belt portion and a second belt portion, each portion of which may be adjusted in length.

It is a further object of the invention to provide a method of adjusting a length of at least one portion of a belt of a back brace.

It is another object of the invention to provide a back brace with a first belt portion and a second belt portion each being secured to a plate that may be tensioned to deform, in order to increase support to the lumbar region of the wearer's back.

It is a further objet of the invention to provide a plate for a back brace belt that may be contoured with a secondary part to provide better contact with the wearer's back when deformed to provide additional support.

It is also an object of the invention to provide a back brace with an improved cord guide arrangement to tension and deform a plate into further contact with the lumbar region of the wearer's back.

Further objects and advantages of the invention will become apparent from the following description and claims, and from the accompanying drawings.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

A back brace may be formed to include a back plate shaped to correspond to a lumbar region of a back of a patient, and first and second flexible belt members each having first and second ends, where the first end of the first and second belt members may be configured to removably and repeatedly secure to first and second end portions of the back plate, respectively, using hook and loop fastening materials. Each of the first and second belt members may be formed to have a common predetermined belt member length, and when secured to the back plate, the brace itself has a stock brace length. In order to secure the brace about the waist of the patient, the second ends of the belt members may be configured to removably and repeatedly secure to each other, e.g., using hook and loop materials, where such hook and loop materials are descriptive names for such materials that are sold under the trademark VELCRO®.

A method for sizing the back brace may begin by forming a flexible elongated measurement member to have a length equaling the stock brace length, and by securing a length of hook material on a first end of the flexible elongated measurement member. A marker may be configured for sliding upon the flexible measurement member, and may have a loop material fixedly secured thereto, which loop material is configured to releasably secure to the hook material on the flexible elongated measurement member.

Next the flexible measurement member may be wrapped around the waist of the patient with its first end overlapping onto an excess amount of the length of the measurement member. The marker may be slid onto the flexible elongated measurement member until contacting the first end of the flexible elongated measurement member, which identifies the excess amount of the brace length. The flexible elongated measurement member is then folded, causing contacting and coupling of the hook material on its first end with the loop material of the marker, with the folded portion of the flexible elongated measurement member identifying an excess length amount for each of the first and second flexible belt members. The first end of the first and second belt members may be disconnected from the back plate, and may be laid upon a flat surface. One end of the folded portion of the flexible elongated measurement member is positioned adjacent to the first end of the first belt member, and is aligned therewith. The first belt member may be cut to remove the excess length amount by cutting proximate to a second end of the folded portion of the flexible elongated measurement member. The same may be done for the second belt member. The first ends of the first and second belt member may then be reconnected to the first and second end portions of the back plate, and the brace may be secured to the waist of the wearer, with a small amount of overlap between the second ends of the first and second belt members.

The above described back brace may also include first and second cords, and a particular cord guide arrangement. The cord guide arrangement may include a left cord plate and a right cord plate, which may be laterally and medially slidably mounted to the left and right sides of the back plate, respectively, and to which the belt members may be secured (e.g., using hook and loop materials), rather than being directly secured to the back plate, as noted above. The left cord plate may include:
- a first upper cord guide, the first upper cord guide positioned on an upper portion of the left cord plate;
- a second upper cord guide, the second upper cord guide positioned concentric to the first upper cord guide;
- a first lower cord guide, the first lower cord guide positioned on a lower portion of the left cord plate; and
- a second lower cord guide, the second lower cord guide positioned concentric to the first lower cord guide.

The right cord plate may include:
- a first upper cord guide, the first upper cord guide of the right cord plate positioned on an upper portion of the right cord plate;
- a second upper cord guide, the second upper cord guide of the right cord plate positioned concentric to the first upper cord guide of the right cord plate;
- a first lower cord guide, the first lower cord guide of the right cord plate positioned on a lower portion of the right cord plate; and
- a second lower cord guide, the second lower cord guide of the right cord plate positioned concentric to the first lower cord guide of the right cord plate.

Each cord guide may be formed of a circular segment that may be about 180 degrees, or may be slightly more than 180 degrees, or may be less than 180 degrees.

The first cord may be sequentially wound around the first upper cord guide of the right cord plate, the first upper cord guide of the left cord plate, the second upper cord guide of the of the right cord plate, the second upper cord guide of the left cord plate, and with a first end of the first cord thereafter secured to the right cord plate.

The second cord may be sequentially wound around the first lower cord guide of the left cord plate, the first lower cord guide of the right cord plate, the second lower cord guide of the of the left cord plate, the second lower cord guide of the right cord plate, and with a first end of the second cord thereafter secured to the left cord plate.

The free ends of the cords may be secured to a respective handle, which handles may be releasably secured to the belt, after tensioning of the brace, using hook and loop materials respectively on the handle and belt.

The concentric cord guide walls with the cord looped around as described above provides a mechanical advantage to buckle the plate to exert a compressive force on the patient's torso, when a load is applied on the two cords simultaneously, by pulling on each cord via the handle by the patient, and thereafter releasably securing the handles to the belt members.

BRIEF DESCRIPTION OF THE DRAWINGS

The description of the various example embodiments is explained in conjunction with appended drawings, in which:

FIG. 1 is a front view of a first embodiment of a back brace disclosed herein;

FIG. 2 is a front view of a measurement apparatus that may be used for adjusting the length of the belt of the back brace of FIG. 1, which may include a flexible elongated member, a marker that may be slidable upon the flexible elongated member, and hook and loop materials with one of each disposed on the marker and upon the end of the flexible elongated member;

FIG. 2A the front view of FIG. 2, showing only the flexible elongated member;

FIG. 9 is the back brace as shown in FIG. 1 without the belt members having been trimmed for the brace to be custom fit for the wearer;

FIG. 10 is the back brace of FIG. 1, but shown after the belt members have been trimmed for the brace to be custom fit for the wearer;

FIG. 11 is an exploded view of the component parts that may be assembled to form another back brace, which is shown with a first embodiment of a height-adjustment member releasably secured at a first position of the deformable back plate;

FIG. 12 shows the component parts of FIG. 11, after being assembled to form the back brace, and being shown with a second embodiment of a height-adjustment member releasably secured at a first position of the deformable back plate;

FIG. 13 is a perspective view showing the deformable back plate and the height-adjustment member of FIG. 12;

FIG. 14 is a side view of the deformable back plate shown in FIG. 13;

FIG. 15 is an enlarged perspective view of an attachment protrusion of the height-adjustment member of FIG. 13;

FIG. 17A shows an alternate structure for the cord guide wall, being formed of a plurality of cylindrical members;

FIGS. 21-24 are a series of perspective views of another back brace embodiment;

DETAILED DESCRIPTION OF THE INVENTION

Figure 4:
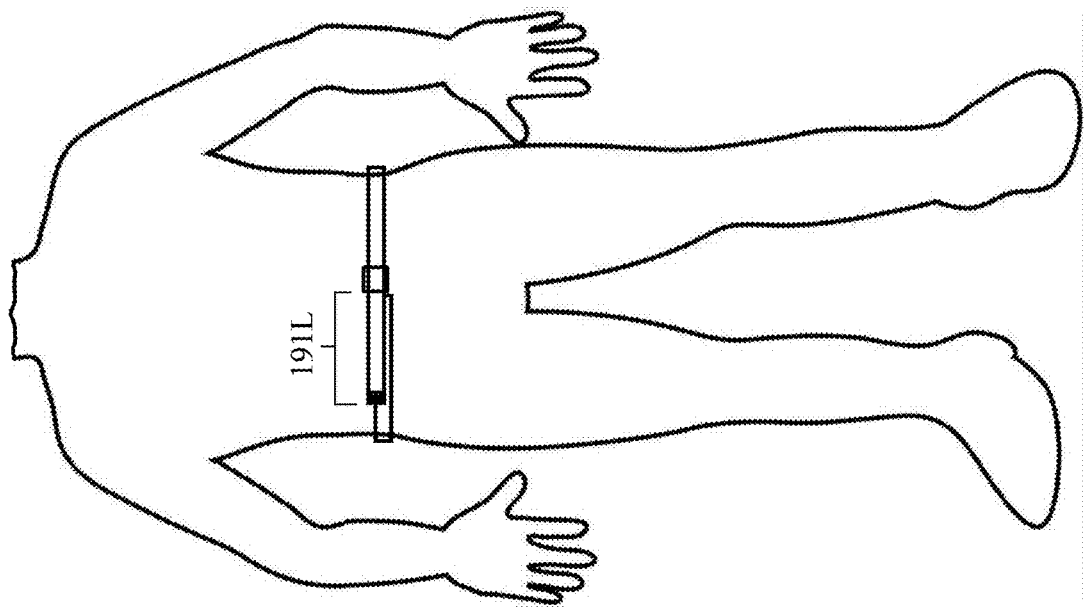
FIG. 4 illustrates the measurement apparatus of FIG. 3 disposed about the waist of a person, but is shown after the marker has been slid to the point indicating the waist measurement.

As used throughout this specification, the word "may" is used in a permissive sense (i.e., meaning having the potential to), rather than a mandatory sense (i.e., meaning must), as more than one embodiment of the invention may be disclosed herein. Similarly, the words "include", "including", and "includes" mean including but not limited to.

The phrases "at least one", "one or more", and "and/or" may be open-ended expressions that are both conjunctive and disjunctive in operation. For example, each of the expressions "at least one of A, B and C", "one or more of A, B, and C", and "A, B, and/or C" herein means all of the following possible combinations: A alone; or B alone; or C alone; or A and B together; or A and C together; or B and C together; or A, B and C together.

Also, the disclosures of all patents, published patent applications, and non-patent literature cited within this document are incorporated herein in their entirety by reference. However, it is noted that citing herein of any patents, published patent applications, and non-patent literature is not an admission as to any of those references constituting prior art with respect to the disclosed apparatus.

Furthermore, the described features, advantages, and characteristics of any particular embodiment disclosed herein, may be combined in any suitable manner with any of the other embodiments disclosed herein.

Additionally, any approximating language, as used herein throughout the specification and claims, may be applied to modify any quantitative or qualitative representation that could permissibly vary without resulting in a change in the basic function to which it is related. Accordingly, a value modified by a term such as "about" is not to be limited to the precise value specified, and may include values that differ from the specified value in accordance with applicable case law. Also, in at least some instances, a numerical difference provided by the approximating language may correspond to the precision of an instrument that may be used for measuring the value. A numerical difference provided by the approximating language may also correspond to a manufacturing tolerance associated with production of the aspect/feature being quantified. Furthermore, a numerical difference provided by the approximating language may also correspond to an overall tolerance for the aspect/feature that may be derived from variations resulting from a stack up (i.e., the sum) of a multiplicity of such individual tolerances.

Any use of a friction fit (i.e., an interface fit) between two mating parts described herein indicates that the opening (e.g., a hole) is smaller than the part received therein (e.g., a shaft), which may be a slight interference in one embodiment in the range of 0.0001 inches to 0.0003 inches, or an interference of 0.0003 inches to 0.0007 inches in another embodiment, or an interference of 0.0007 inches to 0.0010 inches in yet another embodiment, or a combination of such ranges. Other values for the interference may also be used in different configurations (see e.g., "Press Fit Engineering and Design Calculator," available at: www.engineersedge.com/calculators/machine-design/press-fit/press-fit-calculator.htm).

Any described use of a clearance fit indicates that the opening (e.g., a hole) is larger than the part received therein (e.g., a shaft), enabling the two parts to move (e.g. to slide and/or rotate) when assembled, where the gap between the opening and the part may depend upon the size of the part and the type of clearance fit (e.g., for a 0.1250 inch shaft diameter the opening may be 0.1285 inches for a close fit and may be 0.1360 inches for a free (running) fit; and for a 0.5000 inch diameter shaft size the opening may be 0.5156 inches for a close clearance fit and may be 0.5312 inches for a free clearance fit). Other clearance amounts may also be used.

Figure 7:
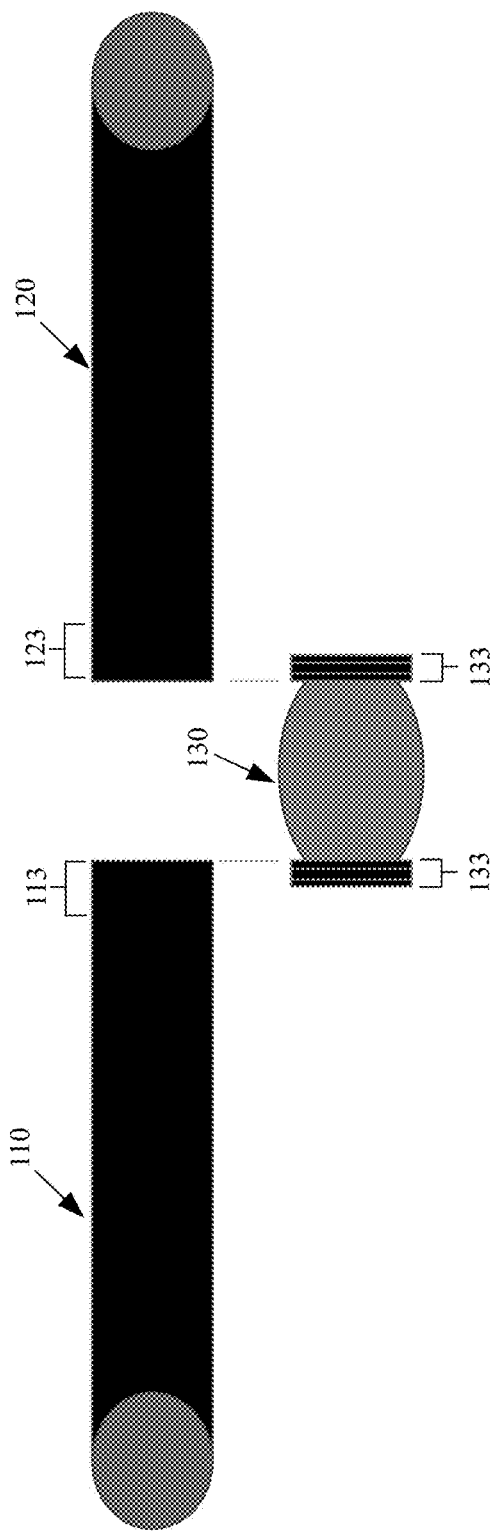
FIG. 7 shows the first and second belt members of the back brace of FIG. 1 after being detached from the central plate assembly.

In accordance with at least one embodiment of the disclosed apparatus, a back brace 100 as shown in FIG. 1 and FIG. 7 may broadly include a first belt member 110, a second belt member 120, and a central plate assembly 130. At least a portion 113 of the first belt member 110 and at least a portion 123 of the second belt member 120 may be formed of a loop material, and the two sides 133 of the central plate assembly 130 may be formed of a hook material (e.g., hook and loop materials that may be sold under the trade name "Velcro") for releasable coupling of the belt members to the central plate assembly. Alternatively, the positioning of the hook and loop materials may be reversed.

FIG. 2 shows a measurement apparatus 190 that may be used in a process for adjusting the length of each of the first belt member 110 and the second belt member 120 of the back brace 100. The measurement apparatus 190 includes: a flexible elongated member 191, a marker 192 configured to slide upon the flexible elongated member, and hook and loop materials with one secured to the marker and one secured to the end of the flexible elongated member (e.g., a hook or loop material 192H/L secured to the marker 192, and a loop or hook material 193L/H secured to the end of the flexible elongated member). The flexible elongated member 191 (FIG. 2A) may be any suitable flexible member that can be wrapped around the waist of the wearer of the back brace 100, including, but not limited to, a string, a flat paper/tape, etc. The length of the flexible elongated member 191 would be substantially the same of the initial length of the back brace 100 as shown in FIG. 1.

Figure 3:
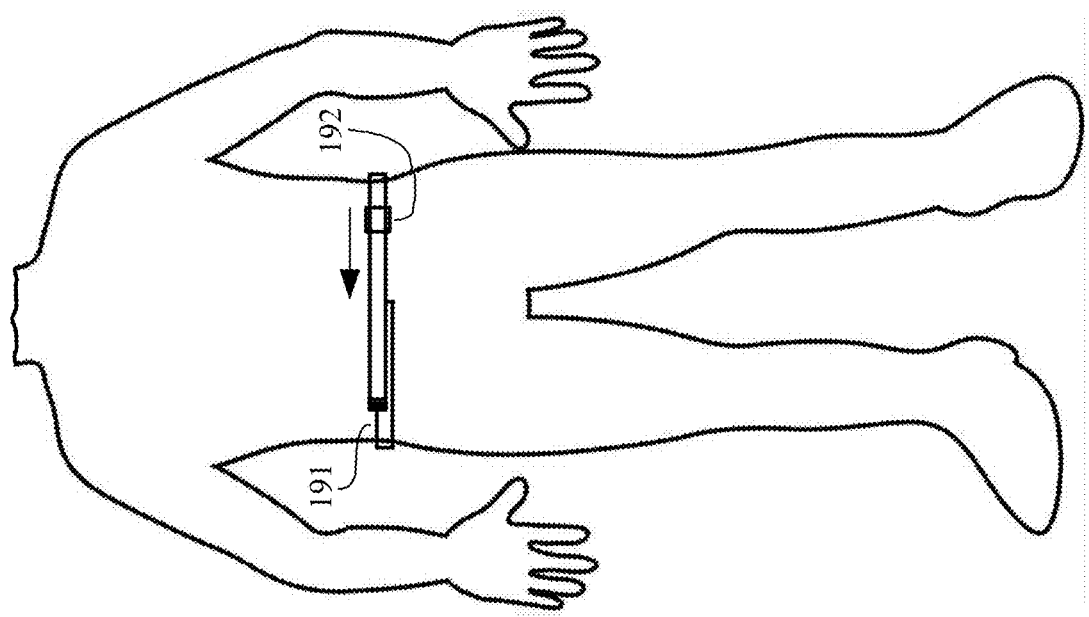
FIG. 3 illustrates the measurement apparatus of FIG. 2 disposed about the waist of a person preparing to adjust the length of the belt of the back brace of FIG. 1.
Figure 5:
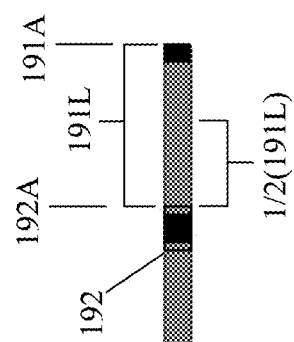
FIG. 5 shows the measurement apparatus of FIG. 4 after being removed from the person's waist.
Figure 6:
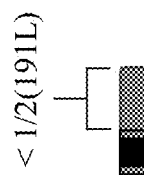
FIG. 6 shows the measurement apparatus of FIG. 5, but after folding over the end of the strip for the hook material located thereat to couple to the loop material on the marker.

The process may begin with the person wrapping the flexible elongated member 191 of the measurement apparatus 190 around his/her waist, as shown in FIG. 3. The person may next slide the marker 192 until it reaches the first end of the flexible elongated member 191, as shown in FIG. 4, which identifies an amount of overlap, i.e., an excess belt length 191L. The measurement apparatus 190 with the marker so positioned to identify the excess belt length 191L is shown in a flattened condition in FIG. 5, after being removed from the person's waist. The flexible elongated member 191 may be folded for the end 191A to just reach the end 192A of the marker 192, so that only half of the excess belt length 191L may extend beyond the marker. However, this would make the adjusted/trimmed belt length exactly the same as the waist of the wearer, and may leave little or no overlap to permit comfortable coupling of the end portion of the first belt member 110 to the end portion of the second belt member 120. Therefore, the flexible elongated member 191 may be folded such that the hook material (or loop material) 193L/H located beginning at the end 191A may be releasably coupled to the loop material (or hook material) 192H/L on the marker 192; so as seen in FIG. 6 the amount of the flexible elongated member 191 that protrudes beyond the marker 192 may be a measured amount less than half of the excess belt length 191L (i.e., the measured amount being roughly one-half of the extent/length of the hook/loop materials on the marker 192). The measured amount may be set to provide sufficient overlap of the end portion of the first belt member 110 with the end portion of the second belt member 120 when the back brace 100 is positioned about the waist of the person. In one embodiment, the measured amount may be between 1.0 inch and 1.5 inches; and in another embodiment, the measured amount may be between 1.5 inch and 2.0 inches; and in yet another embodiment, the measured amount may be between 2.5 inch and 3.0 inches; and in other embodiments, a combination of such ranges or other ranges may alternatively be used.

Figure 8:
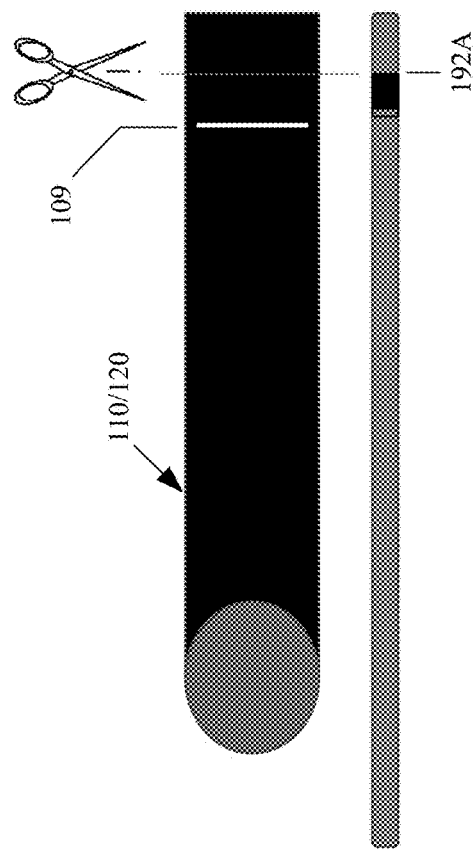
FIG. 8 shows the end of the measurement apparatus aligned with the attachment end of the first belt member, with the marker indicating the amount of material to be cut from the end of the belt member.

Next, the measurement apparatus 190 may be successively positioned adjacent to each of the first belt member 110 and the second belt member 120, so that the folded over end is aligned with the end of the belt members as shown in FIG. 8. The end 192A of the marker 192 identifies the desired location for cutting/trimming of the belt members 110/120, which cutting/trimming may be done using a scissors or other suitable cutting apparatus. The length of the hook material (or loop material) 193L/H located at the end 191A of the flexible elongated member 191 may be formed to be substantially equal to the length of the loop material (or hook material) 192H/L used on the marker 192; so during the above-described folding of the flexible elongated member 191, a substantial entirety of the length the hook material (or loop material) 193L/H at its end 191A may be positioned to overlie a substantial entirety of the loop material (or hook material) 192H/L on the marker 192, as it is coupled thereto.

After both the first belt member 110 and the second belt member 120 have been trimmed, they may each be reattached to the central plate assembly 130 using the hook and loop materials. FIG. 9 shows the original length of the back brace 100 with the untrimmed first and second belt members 110/120, and FIG. 10 shows the length-adjusted back brace 100' with the trimmed first belt member 110' and the trimmed second belt member 120'. Note that FIG. 8 shows that each of the belt members may have a line marking 109 to indicate that such an excessive amount of the belt member is to be trimmed off that a smaller belt member size may preferably be used instead.

To be further illustrative, a numerical example is provided. A final length for the back brace that provides a two inch overlap of the ends of the belts may be desired, which would require the extent of the hook material (or loop material) 193L/H located beginning at the end 191A of the flexible elongated member 191 be two (2) inches in length. Therefore, in the case where the excess length 191L may be 10 inches, the amount that the length of the brace should be shortened would be 8 inches; and thus the amount that the first and second belt members would each need to be shortened is 4 inches. So when the flexible elongated member 191 is folded for the two-inch long hook material (or loop material) 193L/H located beginning at the end 191A to be releasably coupled to the loop material (or hook material) 192H/L on the marker 192, the amount that the flexible elongated member 191 protrudes beyond the marker 192 (see FIG. 8) will be four inches (i.e., the ten inch excess length on the elongated member 191 is reduced by the two inch length of the hook material (or loop material) 193L/H, leaving only a four inch long flattened loop that will serve as a cutting guide to remove four inches off each of the ends of the first and second belt members 110/120).

In another embodiment the person could also use only the flexible elongated member 191, without the marker 192 or the hook material/loop material 193L/H located on the end of the flexible elongated member 191, but the person would have to use his/her fingers to mark the flexible elongated member and then fold it over and hold next to the belt members to identify the trim location.

FIG. 11 is an exploded view of the component parts that may be assembled to form another back brace, which is shown with a first embodiment of a height-adjustment member releasably secured at a first position of the deformable back plate, while FIG. 12 shows the component parts of FIG. 11 after being assembled to form the back brace, and is shown with a second embodiment of a height-adjustment member releasably secured at a first position of the deformable back plate.

The back brace 200 that is shown in FIG. 12 may broadly include a first belt member 210, a second (i.e., right) belt member 220, a central back plate member 230, a first cord plate 240, a second cord plate 250, a first cord 261, a second cord 262, a pair of handle members 270A/270B. As such, the brace 200 may not have a characteristic left side and right side, and may be worn either way by the patient. However, the brace 200 may also include features to support a height-adjustment member 280, which is shown in the exploded view of FIG. 11. Where a height adjustment member such as height adjustment member 280 is utilized on the brace, which is intended to adjust upwardly to provide support to a more elevated portion of the patient's back, one side of the brace may be properly characterized as the left side, and the other side of the brace may be properly characterized as the right side, although such a left/right characterization may be used herein merely to be descriptive, without importing the requirement of an adjustment member into the particularly described and/or claimed brace embodiment.

The central back plate member 230 is shown in detail in FIG. 13 and FIG. 14. As shown therein the central back plate member 230 may be formed to generally match the contours of a person's back, including the curved transitions/inversions moving in a vertical direction from the person's backside to their lumbar region, and up towards the thoracic region of their spine. In addition, the central back plate member 230 may be formed to generally match the lateral contours of a person's body, i.e., the curved transitions moving from the right side, across their spinal region, and over towards their left side. In one embodiment the central back plate member 230 may be formed into several different sizes (e.g., extra-small, small, medium, large, extra-large, double-extra-large, etc.).

The back plate member 230 may also be formed to include several pluralities of distributed openings 230P (e.g., in the upper left quadrant, the upper right quadrant, the lower left quadrant, and the lower right quadrant), which openings may assist in deforming the plate into contact with the wearer's back, as a result of loading imposed by the cords 261/262 and the cord plates 240/250.

The back plate member 230 may also be formed to include at least one pair of openings 231A/231B in one embodiment, and may be formed to include four additional similarly formed pairs of openings in another embodiment, which pair (or pairs) of openings may be configured to receive corresponding pairs of particularly shaped protrusions formed on the height-adjustment member 280, as seen in FIG. 13 and FIG. 15. The shape of the protrusion is shown in detail in FIG. 15, and it may have a trapezoidal shape, with a first angled side (e.g., 281Ai) to accommodate engagement with the respective opening, and a second angled side (e.g., 281Aii) to accommodate disengagement from the respective opening. In one embodiment the back plate member 230 may be formed with only one pair of protrusions (e.g., 281A/281B) that may engage any one of the one or more pairs of openings formed in the height-adjustment member 280, so with, for example, five pairs of openings, the height adjustment member may be positioning in any one of five height-adjusted positions using the single pair of protrusions. (Note that other numbers of pairs of opening other than five may be used to produce other numbers of possible height-adjusted positions). In another embodiment, to provide for a more stable mounting of the height-adjustment member 280 to the back plate member 230, the height-adjustment member may be formed to have two pairs of protrusions (e.g., e.g., 281A/281B, 282A/282B), which four protrusions may engage two pairs of the openings in the back plate member, permitting four height-adjusted positions when five pairs of openings are used. In yet another embodiment, the height-adjustment member may be formed to have three pairs of protrusions (e.g., e.g., 281A/281B, 282A/282B, 283A/283B), as shown in FIG. 13, which six protrusions may engage three pairs of openings in the back plate member, permitting three height-adjusted positions when five pairs of openings are used.

Figure 18:
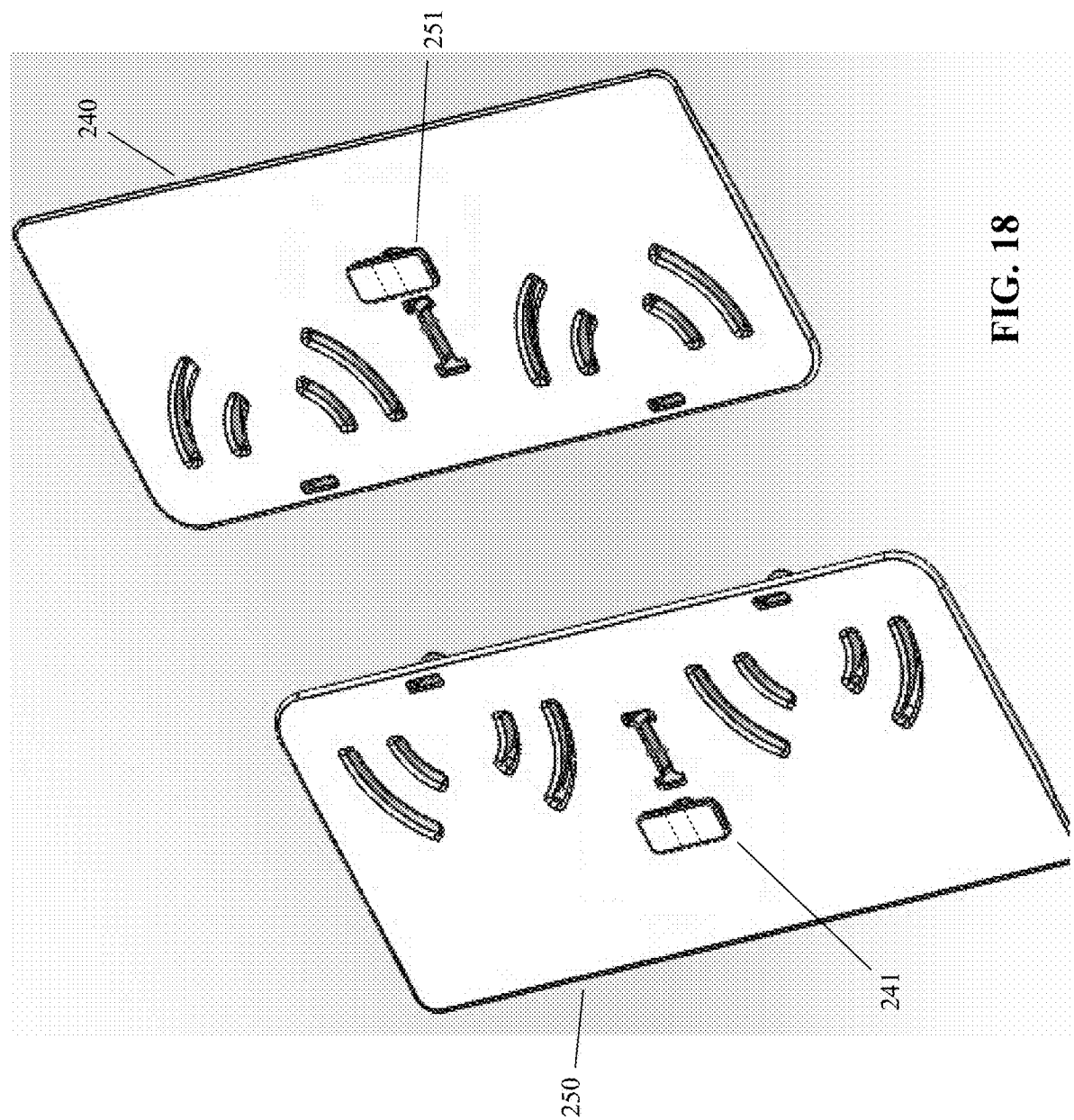
FIG. 18 is a rear perspective view of the two cord guide structures shown in FIG. 13.

The back plate member 230 may also be formed to include a first laterally slotted hole 236 and a second laterally slotted hole 237 (see FIG. 13), which slotted holes may be configured to respectively receive the outstanding leg of the T-shaped protrusions 241/251 formed on the rear side of each of the first cord plate 240 and second cord plate 250, as shown in FIG. 18. The outstanding leg of the T-shaped protrusions may be rounded to permit pivoting of each cord guide member with respect to its slotted hole, or instead may be an elongated rectangular shape to merely permit sliding of each cord guide protrusion within the respective slotted hole.

The first cord plate 240 and the second cord plate 250 may be the same part but which are opposingly mounted with respect to the slotted holes in the back plate member 230. As such, a left-hand part and a right-hand (i.e., a mirror image) part are not necessary, as the same part may be used for the left side and the right side of the brace, by just being rotated 180 degrees. Therefore, the following description proceeds with respect to the first cord plate 240, but is also applicable to the second cord plate 250.

The front side of each cord plate 240 (see FIG. 17) may include a first concentric set of cord guides 241 and a second concentric set of cord guides 242, which second set may be formed the same as the first set. The first concentric sets of cord guides 241 may be formed to include at least a first curved cord guide wall 241A, and a second curved cord guide wall 241B being concentric with respect to the first curved cord guide wall 241A, where each may be substantially semi-circular in shape, or be a portion of a circular shape, and have different radii but which both originate at (i.e., are centered upon) substantially the same axial location (i.e., being substantially concentric). It is also noted that each curved wall need not be a full semi-circular wall portion (i.e., being 180 degrees of arc) or a single circular wall portion being less than 180 degrees, and could be made of a plurality of semi-circular wall portions (e.g., each may be formed of two curved wall portions formed with 85 degrees of arc with a five degree spacing therebetween). Also, in another embodiment, a cord guide arrangement other than a "wall" that may smoothly turn the direction of the cord 180 degrees may be formed by a plurality of cylindrical members or other shaped members (see FIG. 17A).

The second concentric sets of cord guides 242 may similarly be formed to include at least a first curved cord guide wall 242A, and a second curved cord guide wall 242B being concentric with respect to the first curved cord guide wall 242A.

Figure 16:
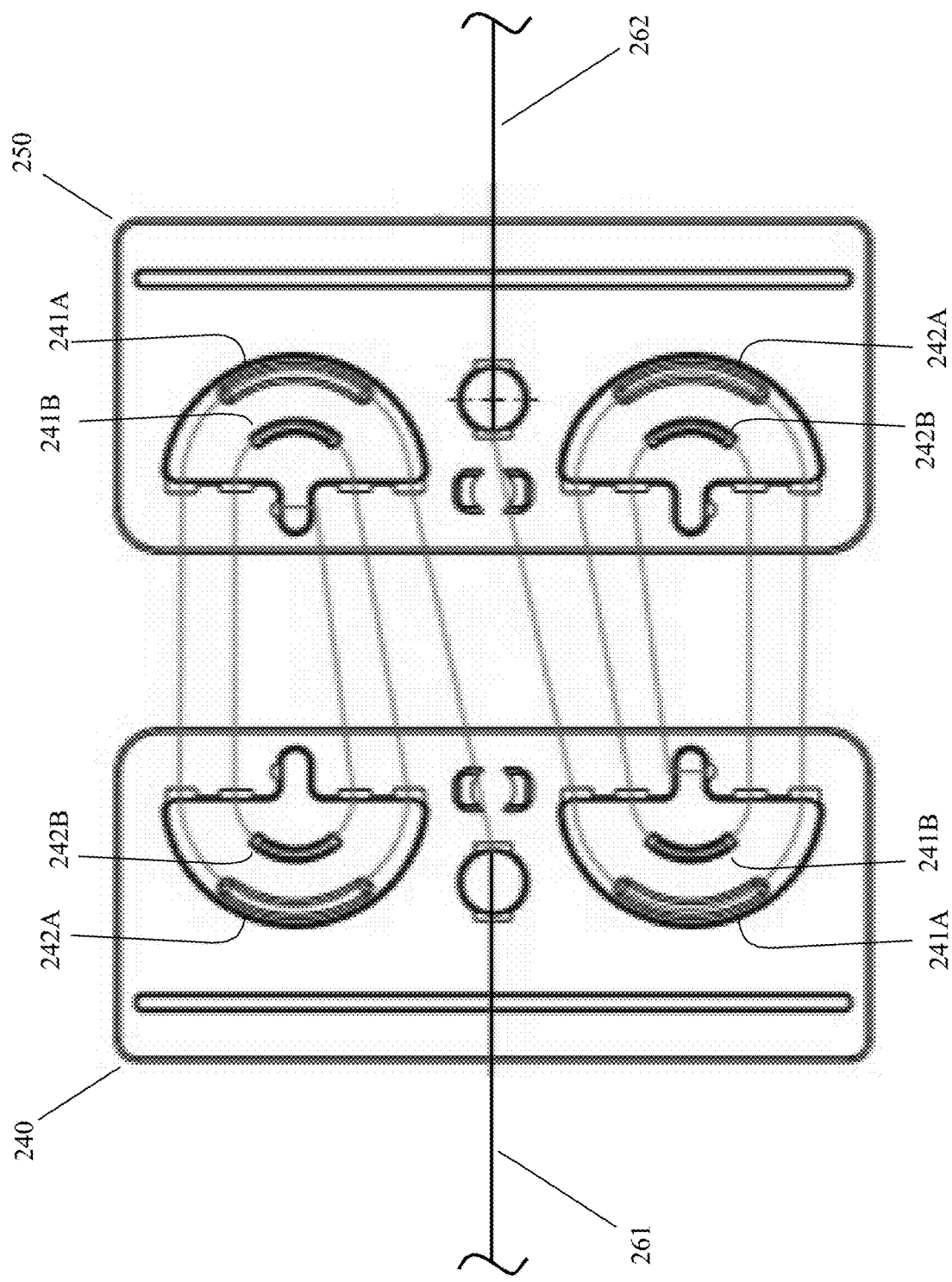
FIG. 16 is an enlarged front view of the cords and the concentric cord guide arrangement of the back brace of FIG. 12.
Figure 17:
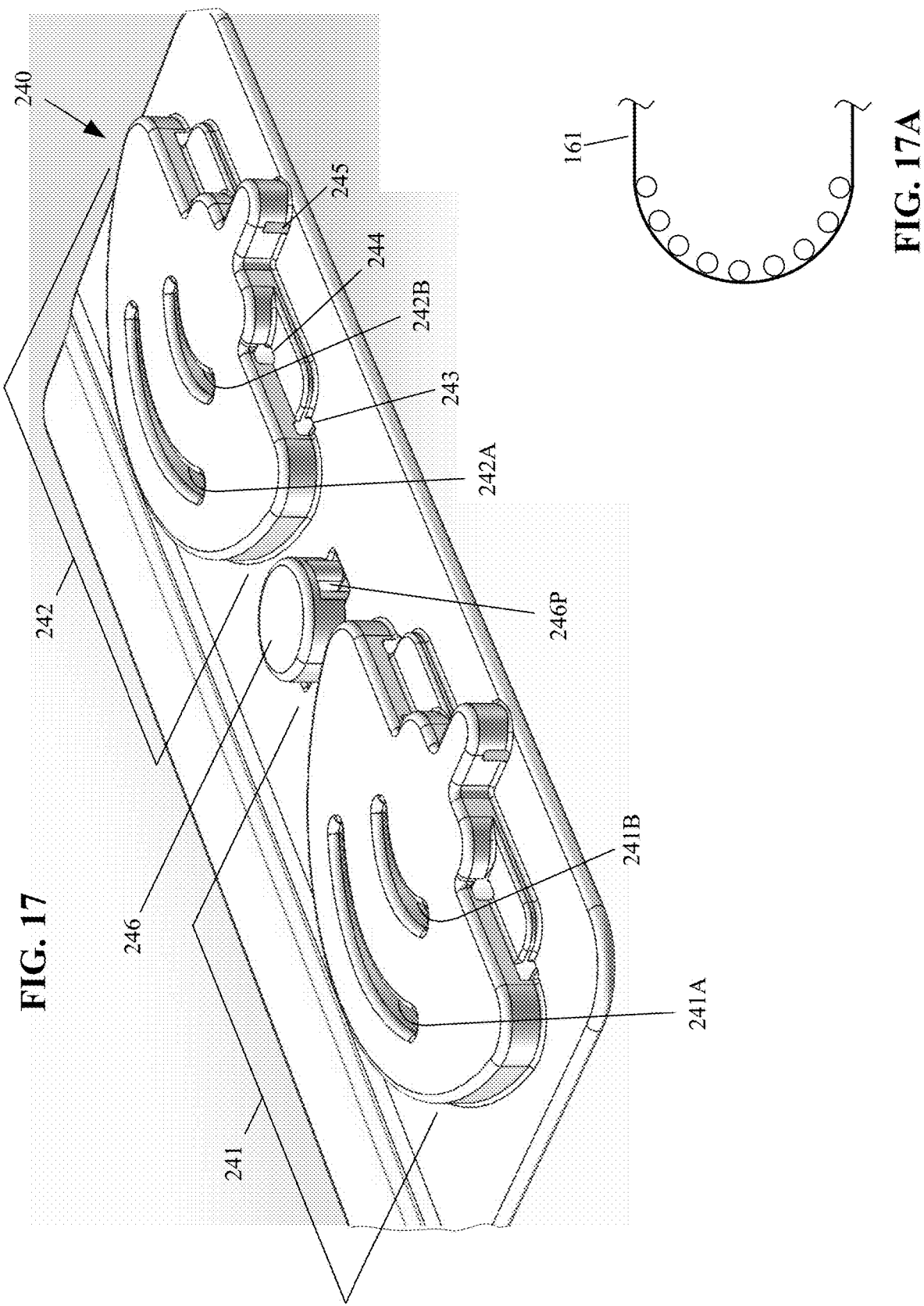
FIG. 17 is a front perspective view of one of the cord guide structures shown in FIG. 13.

To prevent detaching of the cords 261/262 from the curved walls 241/242, each of the cord guides 240A/240B may be formed to generally enclose the curved walls, as seen in FIG. 17, and may also be provided with a series of openings to permit entry/exit of the cord (i.e., openings 243 and 244), and openings to assist in threading of the cord through the cord guides. An opening 245 may also be provided for securing of the first end of the cord thereto (i.e., being looped through and tied off-see FIG. 16), although other methods of securing the cord thereto may alternatively be used, including, but not limited to, adhesive bonding, a mechanical fastener, etc. The first end of each cord may preferably be secured proximate to the center of the curved cord guide walls (i.e., the origin of the radius).

The front side of each cord plate 240/250 (see FIG. 17) may include a protrusion 246 that may have a through-opening 246P oriented substantially perpendicular to a direction being between a center of each of the upper and lower cord guides of the respective left and right cord plate, which may be used to further guide the cord after exiting the concentric set of cord guides 240A/240B, as shown in FIG. 16.

As seen in FIG. 16, the first cord 261 may sequentially loop around the cord guide wall 241A of the right cord plate 250, the cord guide wall 242A of the left cord plate 240, the concentric cord guide wall 241B of the right cord plate, the concentric cord guide wall 242B of the left cord plate, and with a first end of the second cord thereafter being secured to the right cord plate 250; similarly, the second cord 262 may sequentially the cord guide wall 241A of the left cord plate 240, the cord guide wall 242A of the right cord plate 250, the concentric cord guide wall 241B of the left cord plate, the concentric cord guide wall 242B of the right cord plate, and with a first end of the second cord thereafter being secured to the left cord plate 250.

The concentric cord guide walls with the cord looped around as described provide a mechanical advantage to buckle the plate to exert a compressive force on the patient's torso, when a load is applies on the two cords simultaneously, by pulling on each cord by the patient.

Figure 20A:
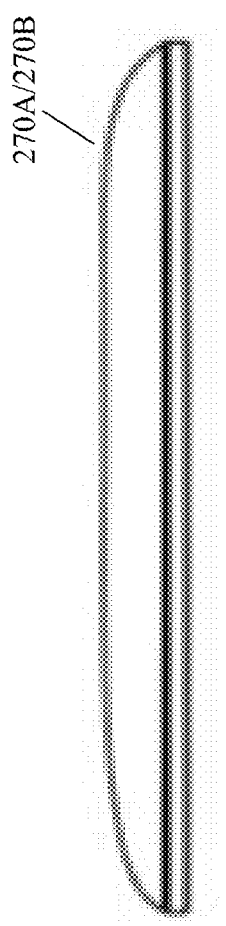
FIG. 20A is a side view of the handle shown in FIG. 19.
Figure 20B:
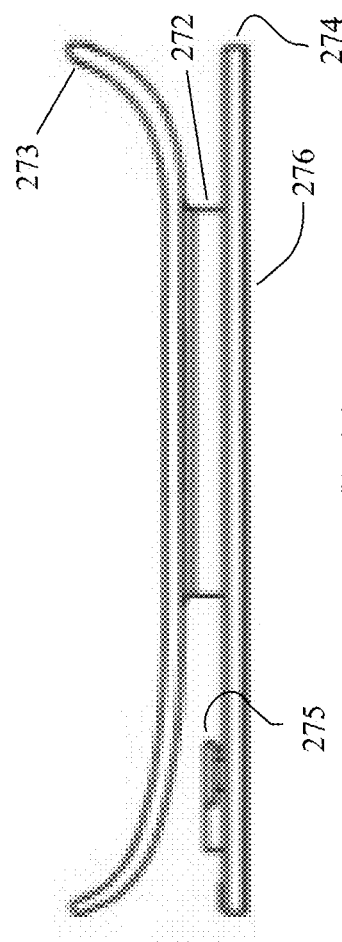
FIG. 20B is the side view of FIG. 20A, but shown with the cover portion deformed upwards to expose the interior.
Figure 19:
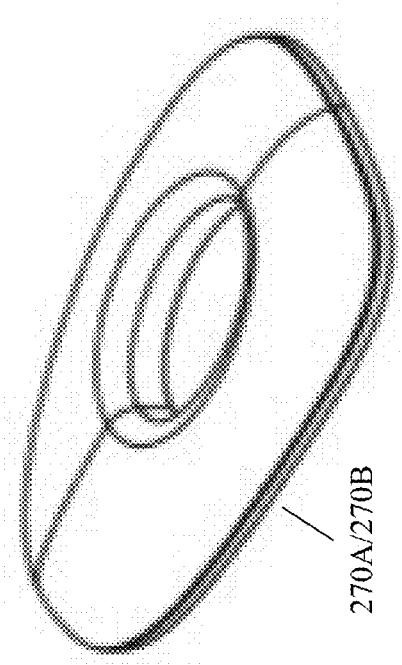
FIG. 19 is a perspective view of the handle for the cord with an oval thumb hole, as shown in FIG. 12.
Figure 25:
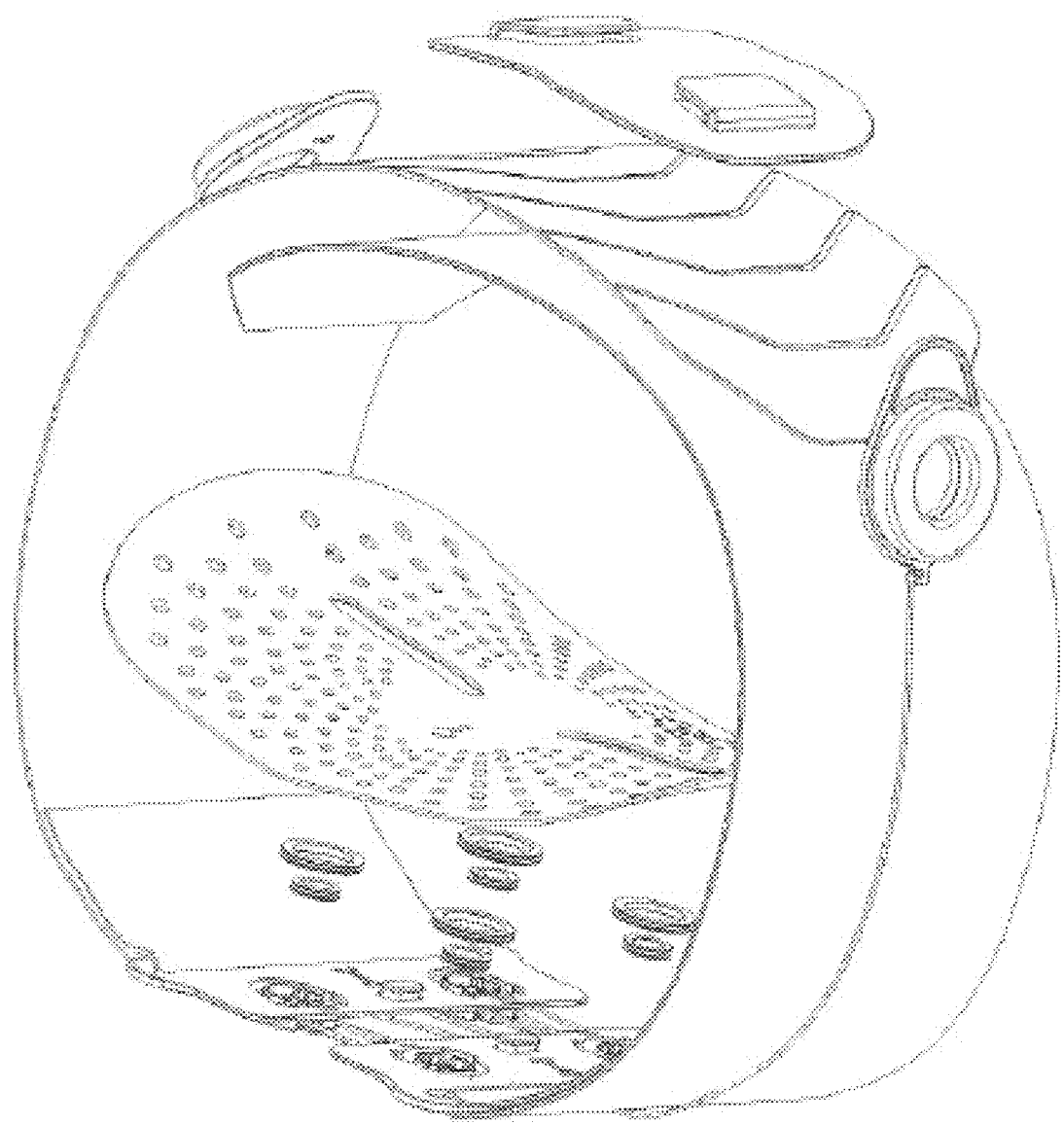
FIG. 25 is an exploded view of the component parts of the back brace of FIGS. 21-24.
Figure 27:
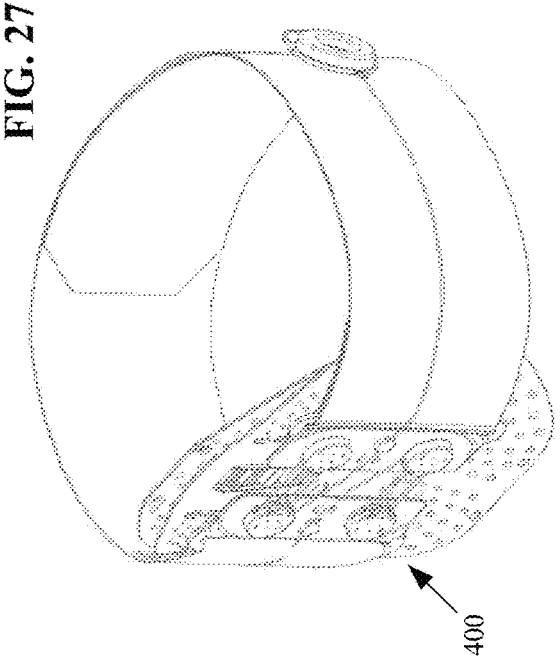
FIGS. 26-29 are a series of perspective views of yet another embodiment of a back brace with a deformable back plate and a height-adjustment member.
Figure 29:
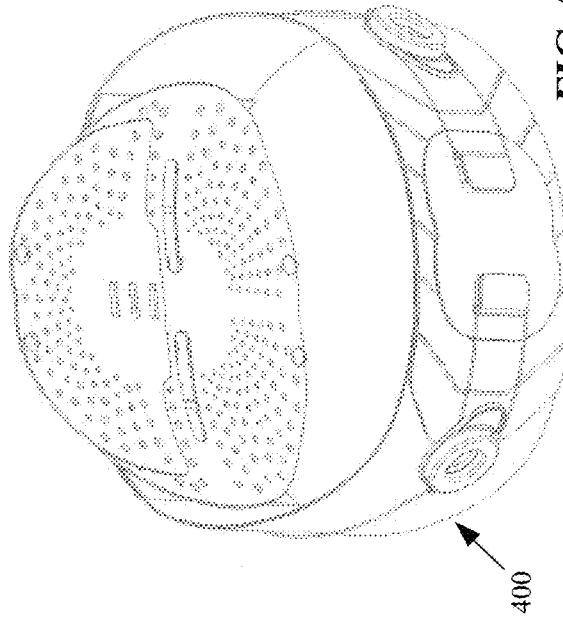
Figure 26:
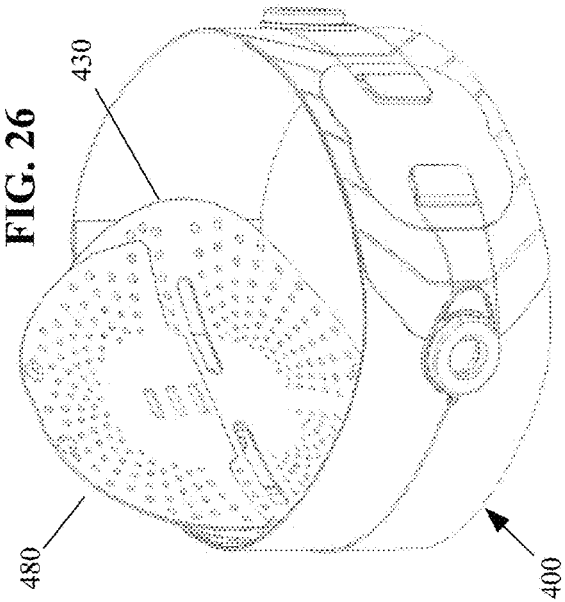
Figure 28:
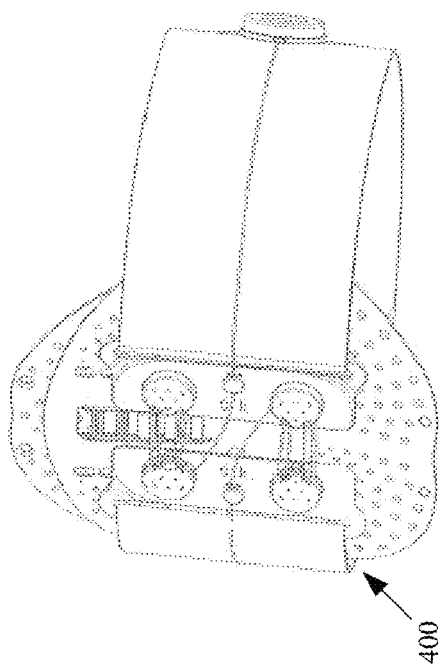
Figure 30B:
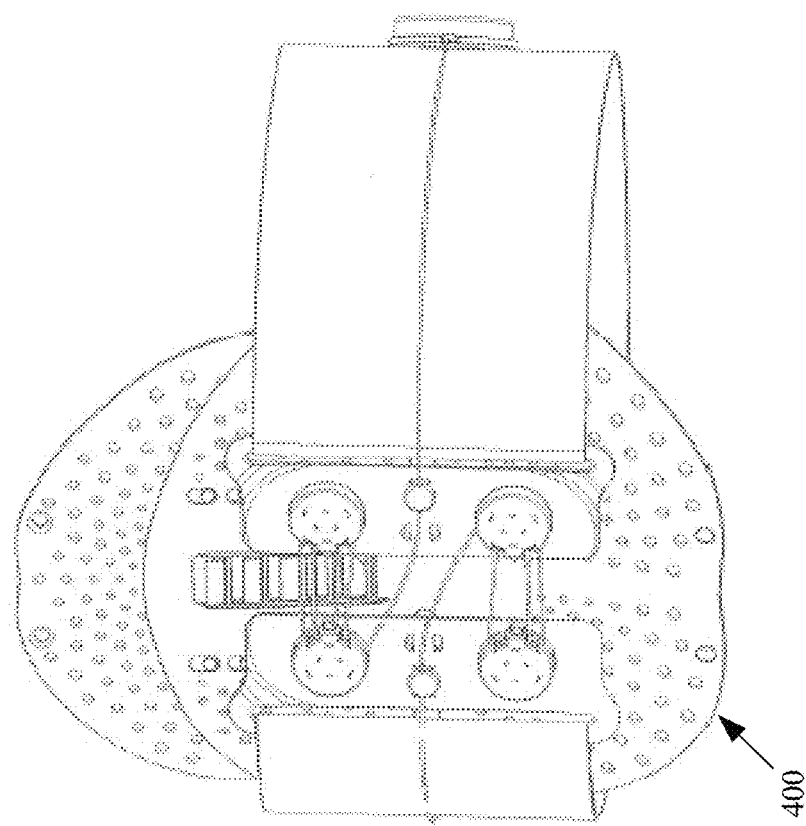
FIGS. 30A-30B show the back brace of FIGS. 26-29 with the height adjustment member being positioned respectively at first and second heights.
Figure 30A:
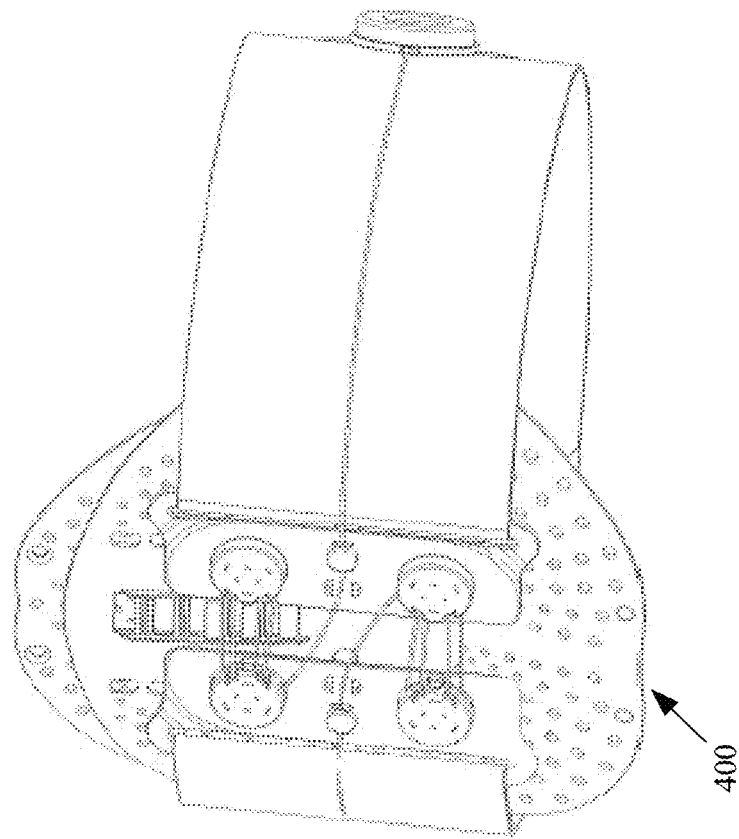
Figure 31:
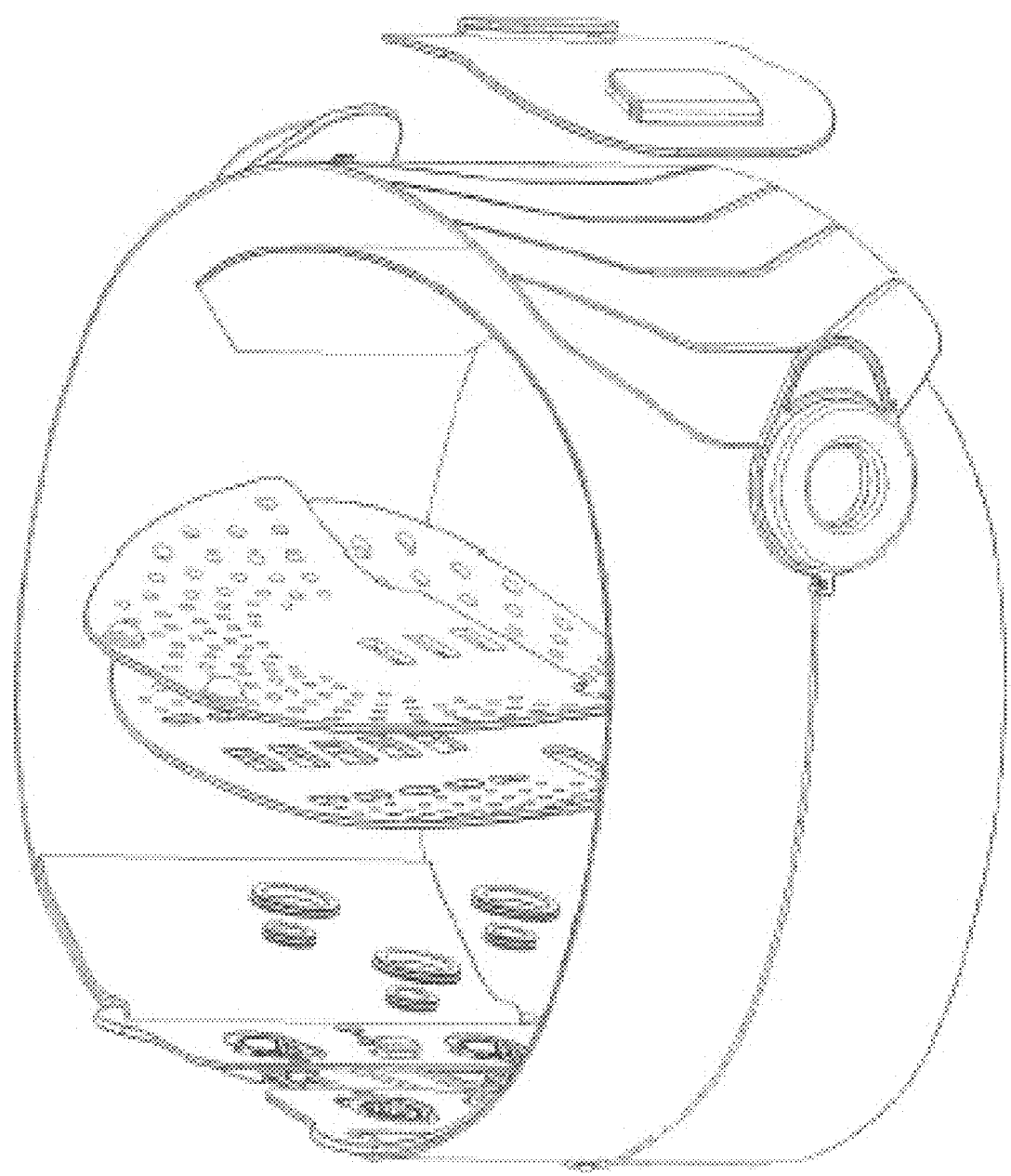
FIG. 31 is an exploded view of the component parts of the back brace of FIGS. 26-29.
Figure 32:
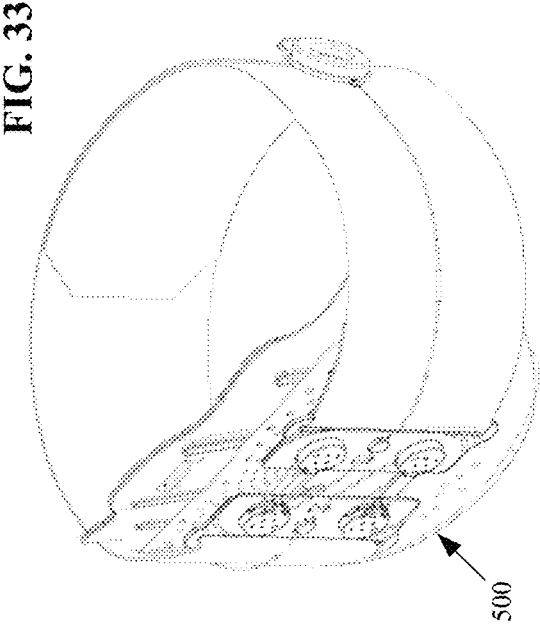
FIGS. 32-36 are a series of perspective views of yet a different embodiment of a back brace with a deformable back plate and a height-adjustment member that is slidably coupled to the back plate using a pair of protrusions on the height-adjustment member and corresponding slots on the back plate.
Figure 33:
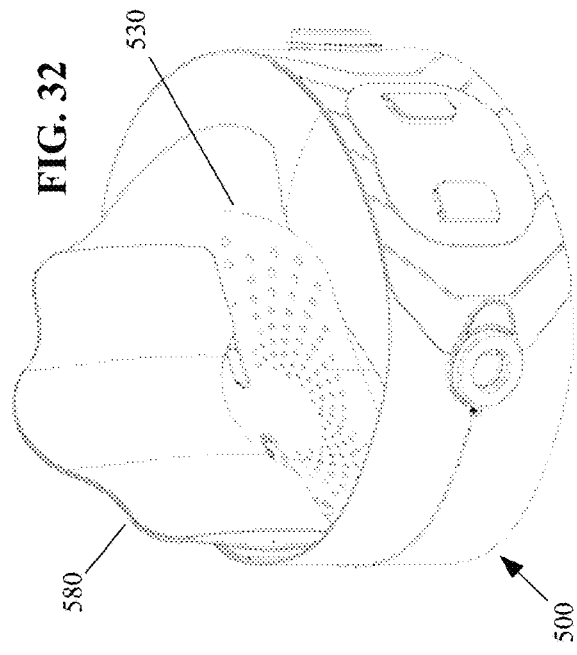
Figure 34:
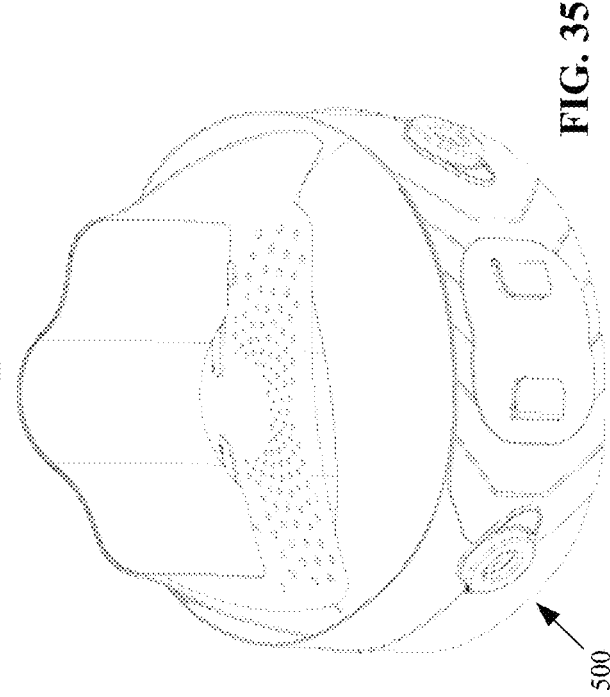
Figure 35:
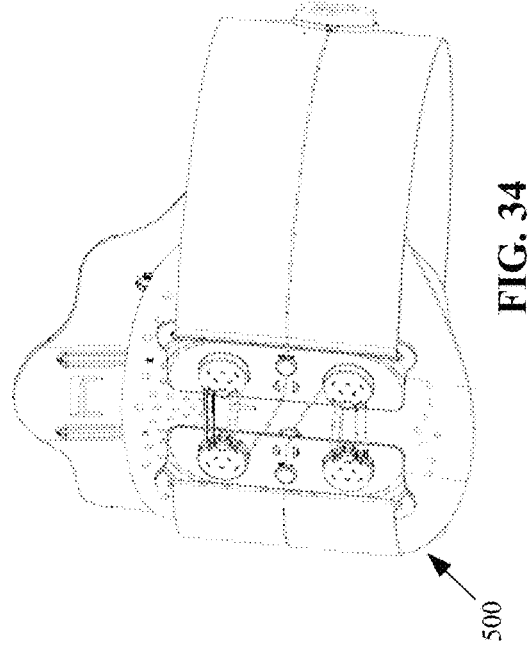
Figure 36:
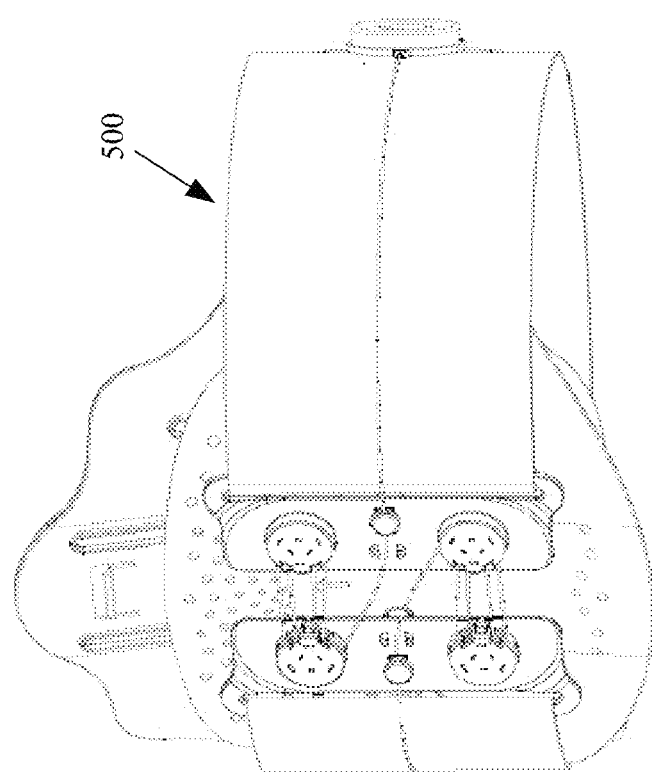

The second end of each of the first cord 261 and second cord 262 may be coupled to the respective handle member 270A/270B for easier pulling of the cords by the patient. Each handle member may be formed as shown in FIG. 19 and FIGS. 20A-20B. The handle members may be formed to include a base 271, an upstanding leg 272 about which the cord may be wrapped, and a cover member 273, which may be made of a flexible material, such that it may normally overlie the wrapped cord but may flex to be deformed away from the base as shown in FIG. 20B. The flexible cover member is configured to flex into contact with said base, and to be deformed away from said contact by winding of the respective cord therebetween and about said leg. The second end of the cord may be secured to the handle in any suitable manner, including, but not limited to, the methods described hereinabove with respect to attachment of the first end of the cord to the cord plates 240/250. Alternatively or additionally, the base 271 may be formed with a post 275 to which the second end of the cord may be secured/tied. The exterior side of the base may have a hook material formed thereon or positioned thereon to permit its releasable attachment to the belt members 210/220, as seen in FIG. 12.

Each side of the cord plates 240/250 opposite the cord entry/exit openings 243/244 may also have a respective piece of hook material 240H/250H formed thereon or secured thereon (see FIG. 11) to permit respective and releasable attachment thereto of the belt members 210/220. The hook material 240H/250H may be wide enough to permit some secondary adjustment to the length of the back brace 100, apart from the cutting/trimming process described above.

FIGS. 21-24 show a series of perspective views of a back brace 300.

FIGS. 26-30B show a series of perspective views of a back brace 400 that is formed similar to the brace 300, but which also includes a height-adjustment member 480 that may adjustably attach to the central back plate member 430 the same as for brace 200.

FIGS. 32-36 are a series of perspective views of a back brace 500 that is formed similar to the back brace 400, but where the height-adjustment member 580 is slidably coupled to the back plate 530 using a pair of protrusions on the height-adjustment member that are slidably received in corresponding slots on the back plate.

Figure 37:
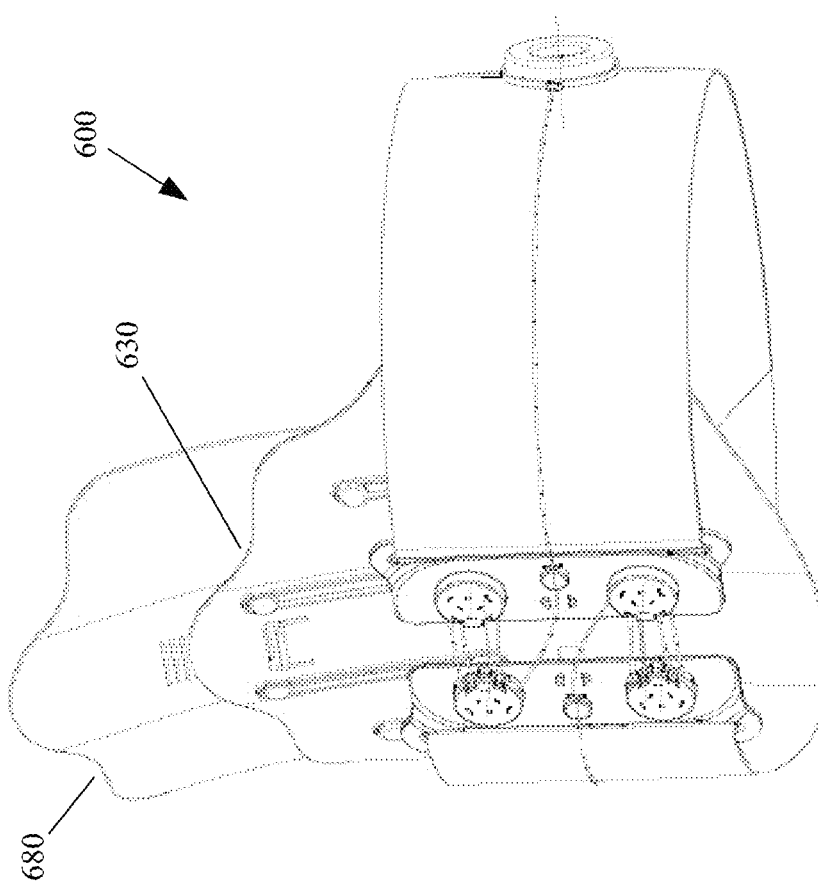
FIG. 37 shows another back brace embodiment having a taller back plate, and a height adjustment member slidably coupled thereto, and thereby being positionable at a plurality of different heights.
Figure 37A:
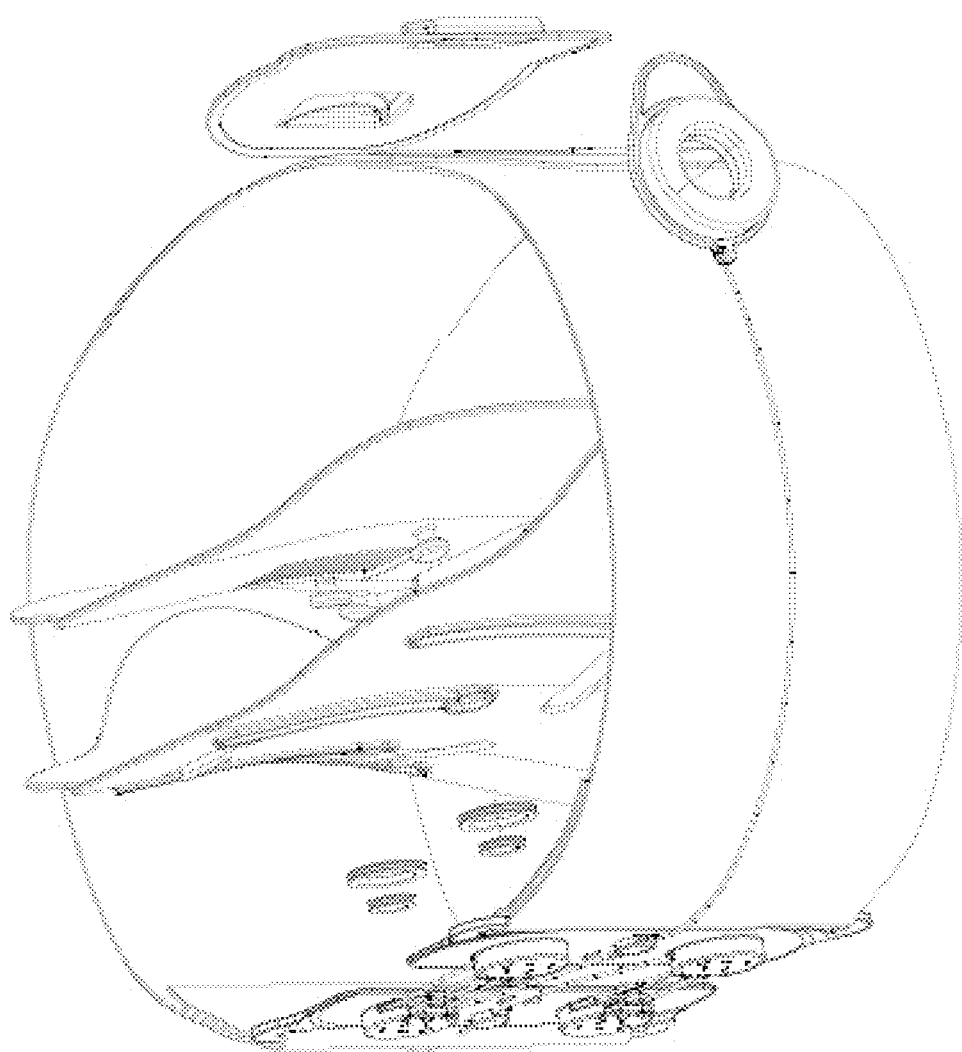
FIG. 37A is an exploded view of the component parts of the back brace of FIG. 37.
Figure 39:
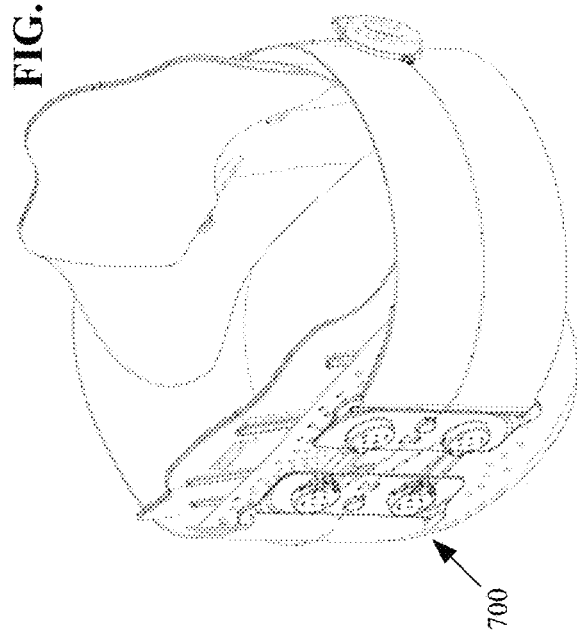
FIGS. 38-41 show a series of perspective views of a torso brace that has a deformable back plate with a height-adjustment member, and a front plate that has its own height adjustment member and are formed similar to the back plate and back adjustment member.
Figure 41:
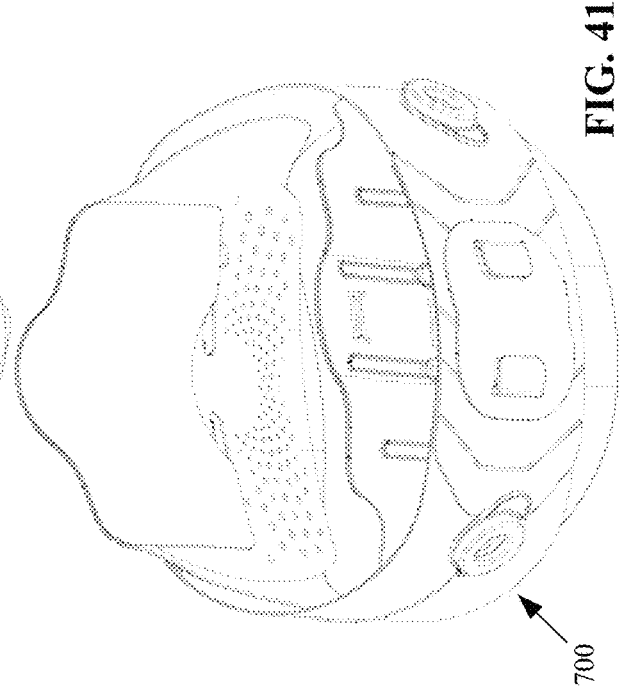
Figure 38:
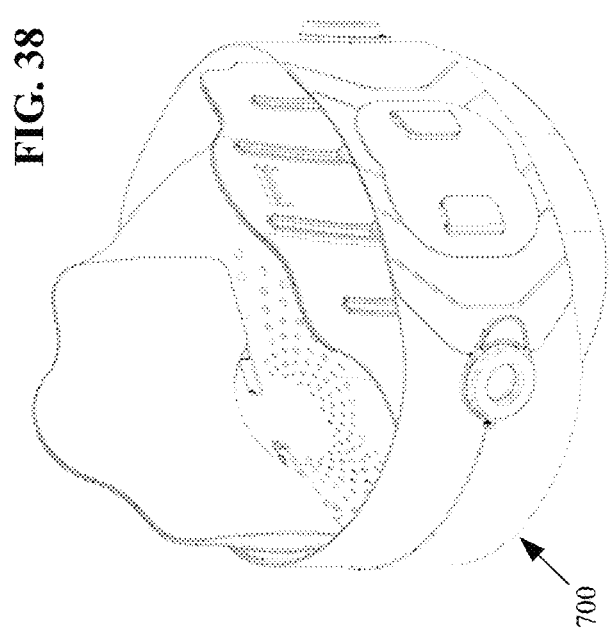
Figure 40:
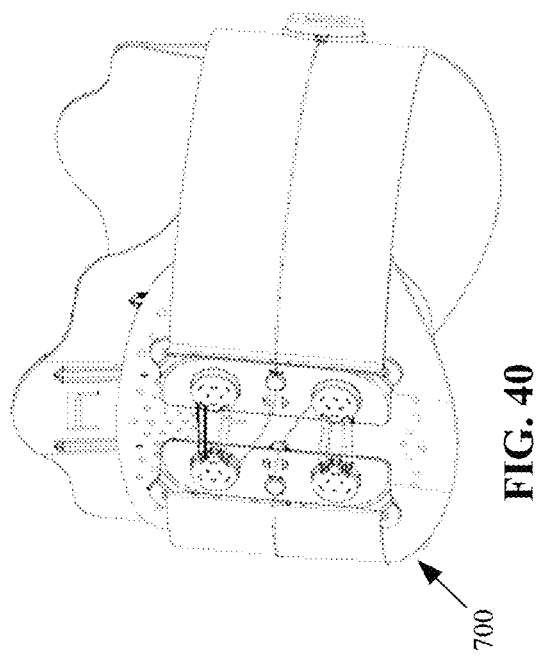

FIG. 37 shows a back brace 600 that is formed similar to brace 500, but which has a taller back plate 630, and has a height adjustment member 680 slidably coupled thereto to be positionable at a plurality of different heights.

Figure 42B:
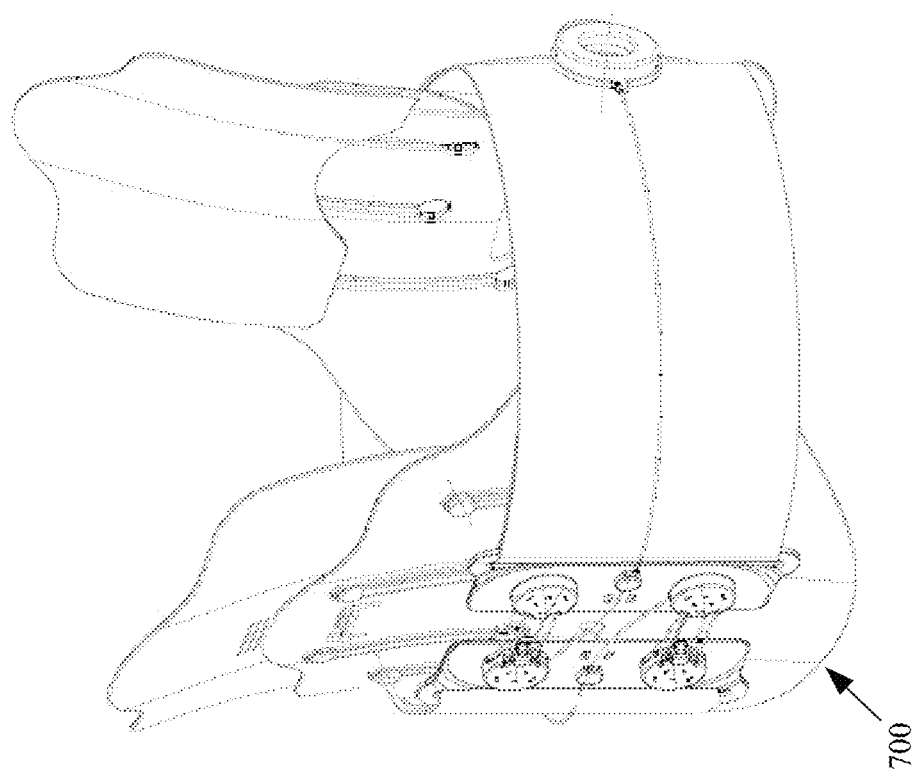
FIGS. 42A-42B show the torso brace of FIGS. 38-41, but with each of the two height adjustment members being positioned respectively at first and second heights.
Figure 42A:
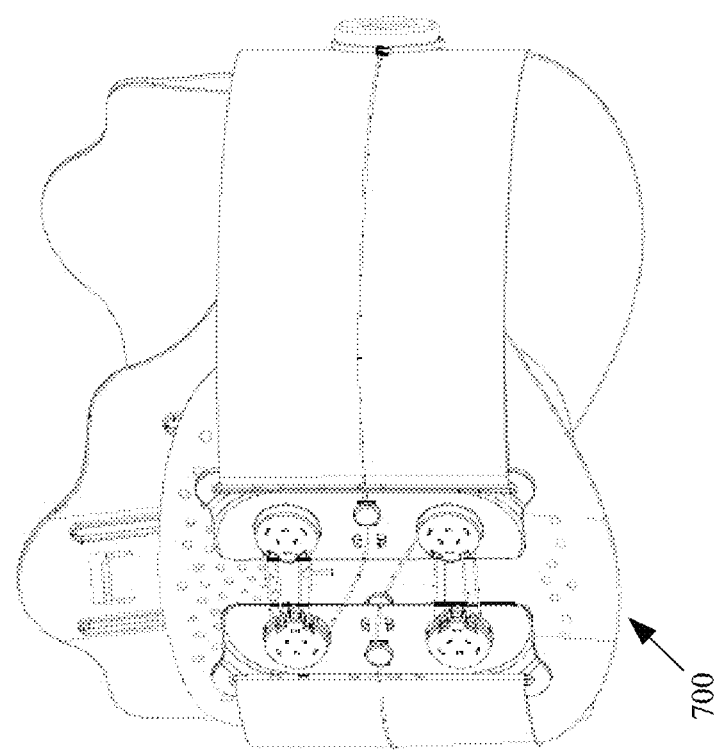
Figure 43:
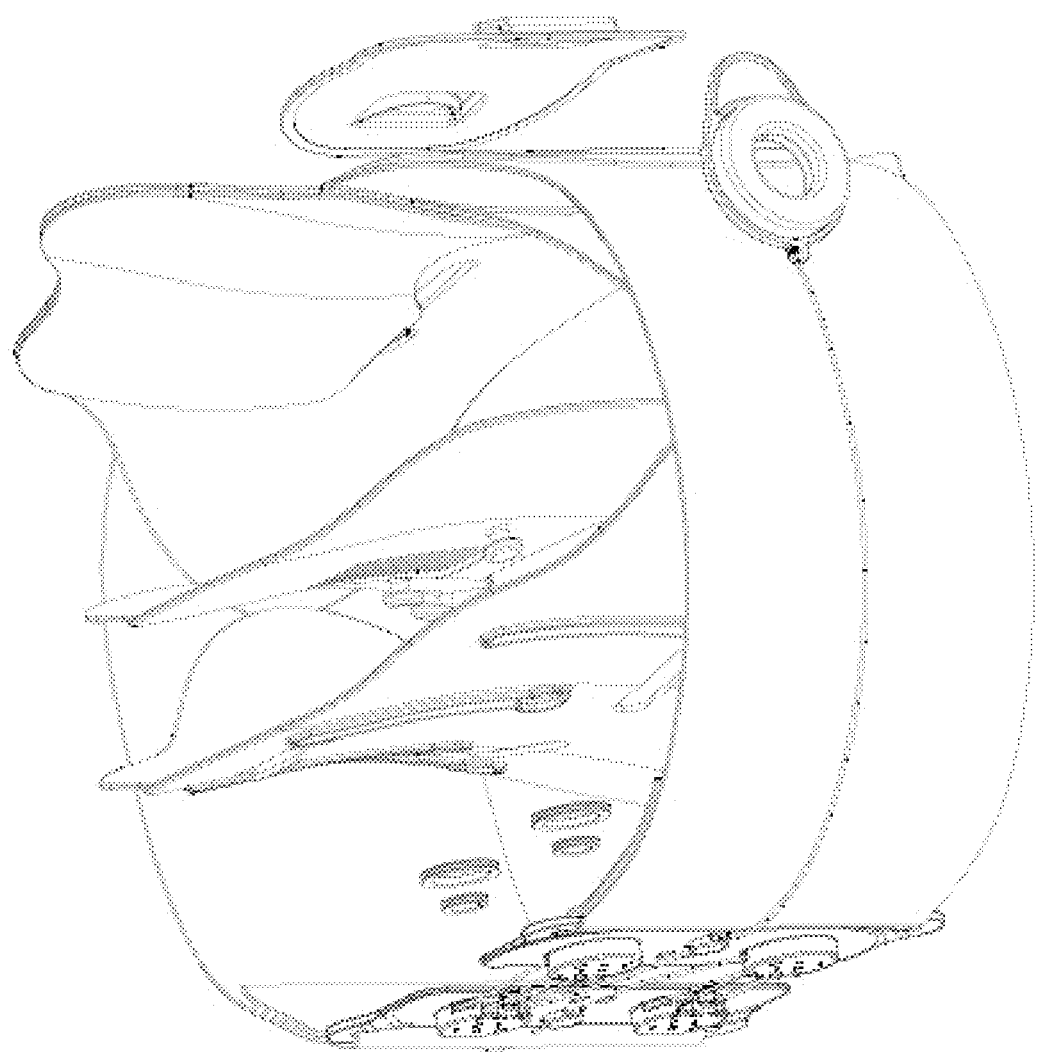
FIG. 43 is an exploded view of the component parts of the torso brace of FIGS. 38-41.

FIGS. 38-41 show a torso brace 700 that has a deformable back plate with a height-adjustment member, and a front plate that has its own height adjustment member, each of which adjustment plates may be formed similar to the back plate and height adjustment member of brace 500. FIGS. 42A-42B show the torso brace 700 with the height adjustment member being positioned respectively at first and second heights.

The sliding fit between each adjustment member and corresponding back plate may be accomplished using a slight friction fit.

While illustrative implementations of one or more embodiments of the disclosed apparatus are provided hereinabove, those skilled in the art and having the benefit of the present disclosure will appreciate that further embodiments may be implemented with various changes within the scope of the disclosed apparatus. Other modifications, substitutions, omissions and changes may be made in the design, size, materials used or proportions, operating conditions, assembly sequence, or arrangement or positioning of elements and members of the exemplary embodiments without departing from the spirit of this invention.

Accordingly, the breadth and scope of the present disclosure should not be limited by any of the above-described example embodiments, but should be defined only in accordance with the following claims and their equivalents.

What is claimed is:

1. A back brace comprising:
   a back plate;
   a left cord plate slidably coupled to a left side of said back plate to slide laterally and medially; said left cord plate comprising:
     a first upper cord guide, said first upper cord guide positioned on an upper portion of said left cord plate;
     a second upper cord guide, said second upper cord guide positioned concentric to said first upper cord guide;
     a first lower cord guide, said first lower cord guide positioned on a lower portion of said left cord plate;
     a second lower cord guide, said second lower cord guide positioned concentric to said first lower cord guide;
   a right cord plate slidably coupled to a right side of said back plate to slide laterally and medially; said right cord plate comprising:
     a first upper cord guide, said first upper cord guide of said right cord plate positioned on an upper portion of said right cord plate;
     a second upper cord guide, said second upper cord guide of said right cord plate positioned concentric to said first upper cord guide of said right cord plate;
     a first lower cord guide, said first lower cord guide of said right cord plate positioned on a lower portion of said right cord plate;
     a second lower cord guide, said second lower cord guide of said right cord plate positioned concentric to said first lower cord guide of said right cord plate;
   a first cord; wherein said first cord sequentially winds around said first upper cord guide of said right cord plate, said first upper cord guide of said left cord plate, said second upper cord guide of said right cord plate, said second upper cord guide of said left cord plate, and with a first end of said first cord thereafter secured to said right cord plate;

a second cord; wherein said second cord sequentially winds around said first lower cord guide of said left cord plate, said first lower cord guide of said right cord plate, said second lower cord guide of said left cord plate, said second lower cord guide of said right cord plate, and with a first end of said second cord thereafter secured to said left cord plate;

a first flexible belt member; a first end of said first flexible belt member secured to a left side of said left cord plate;

a second flexible belt member; a first end of said second flexible belt member secured to a right side of said right cord plate;

means for releasably securing a second end of said first flexible belt member to a second end of said second flexible belt member.

2. The back brace according to claim 1, wherein each said cord guide comprises a circular segment.

3. The back brace according to claim 2, wherein said circular segment of each said cord guide is 180 degrees or less.

4. The back brace according to claim 3,
wherein a second end of said first cord is attached to a first handle; and
wherein a second end of said second cord is attached to a second handle.

5. The back brace according to claim 4,
wherein said left cord plate comprises a protrusion positioned between its upper and lower cord guides, said protrusion comprising a hole oriented substantially perpendicular to a direction being between a center of each of its upper and lower cord guides, with a portion of said first cord between said winding around said first upper cord guide of said right cord plate and said first handle passes through said hole; and
wherein said right cord plate comprises a protrusion positioned between its upper and lower cord guides, said protrusion of said right cord plate comprising a hole oriented substantially perpendicular to a direction being between a center of each of its upper and lower cord guides, with a portion of said second cord between said winding around said first lower cord guide of said left cord plate and said second handle passes through said hole.

6. The back brace according to claim 5, wherein each said handle comprises:
a base;
a leg configured to protrude away from a center of a first side of said base to a distal end;
a flexible cover member, said flexible cover member secured to said distal end of said leg, said flexible cover member configured to flex into contact with said base, and to be deformed away from said contact by winding of the respective cord therebetween and about said leg.

7. The back brace according to claim 6, further comprising a vertical adjustment plate configured to be positioned to said back plate at a plurality of different positions.

8. The back brace according to claim 7, wherein said vertical adjustment plate is slidable with respect to said back plate.

9. The back brace according to claim 7, wherein said vertical adjustment plate is releasably coupled to said back plate by protrusions on said vertical adjustment plate being received within corresponding openings on said back plate.

10. The back brace according to claim 7, further comprising a front plate secured to one of said flexible belt members.

11. The back brace according to claim 6, wherein each said handle comprises hook material configured to be releasably secured to loop material on a respective said belt member.

12. The back brace according to claim 3,
wherein said first end of said first cord is secured to said right cord plate in proximity to a center of said circular upper cord guides of said right cord plate; and
wherein said first end of said second cord is secured to said left cord plate in proximity to a center of said circular lower cord guides of said left cord plate.

13. A method for sizing a back brace, the back brace including: a back plate shaped to correspond to a lumbar region of a back of a patient, and first and second flexible belt members each having first and second ends, the first end of the first and second belt members configured to removably and repeatedly secure to first and second end portions of the back plate, respectively, using hook and loop fastening materials, each of the first and second belt members having a predetermined belt member length, and when secured to the back plate, the brace having a predetermined brace length, the sizing method comprising the steps of:
forming a flexible elongated measurement member having a length equaling the predetermined brace length, and securing a length of hook material on a first end of the flexible elongated measurement member;
forming a marker for sliding upon said flexible elongated measurement member, and securing a loop material to the marker;
wrapping the flexible elongated measurement member around the waist of the patient with its first end overlapping onto an excess amount of the length of the measurement member;
sliding the marker until contacting a second end of the flexible elongated measurement member for identifying an excess amount of the brace length;
folding a portion of the flexible elongated measurement member causing contacting and coupling of the hook material on its first end with the loop material of the marker, with the folded portion of the flexible elongated measurement member identifying an excess length amount for each of the first and second flexible belt members;
disconnecting the first ends of the first and second belt members from the back plate;
positioning one end of the folded portion of the flexible elongated measurement member adjacent to the first end of each of the first and second belt members, and cutting the excess length amount of each of the first and second flexible belt members from the first end of each of the first and second belt members by cutting proximate to a second end of the folded portion of the flexible elongated measurement member;
reconnecting the first ends of the first and second belt member to the first and second end portions of the back plate.

14. The method for sizing a back brace according to claim 13, further comprising the steps of:
forming a length of the loop material of the marker equaling a length of the hook material of the flexible elongated measurement member; and overlaying a substantial entirety of the length of the loop material of the marker onto the length of the hook material of the flexible elongated measurement member during said coupling.

\* \* \* \* \*